United States Patent
Bykanov et al.

(10) Patent No.: US 9,544,984 B2
(45) Date of Patent: Jan. 10, 2017

(54) SYSTEM AND METHOD FOR GENERATION OF EXTREME ULTRAVIOLET LIGHT

(71) Applicant: KLA-Tencor Corporation, Milpitas, CA (US)

(72) Inventors: Alexander Bykanov, San Diego, CA (US); Oleg Khodykin, San Diego, CA (US); Daniel C. Wack, Fredericksburg, VA (US); Konstantin Tsigutkin, San Diego, CA (US); Layton Hale, Castro Valley, CA (US); Joseph Walsh, Soquel, CA (US); Frank Chilese, San Ramon, CA (US); Rudy F. Garcia, Union City, CA (US); Brian Ahr, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/335,442

(22) Filed: Jul. 18, 2014

(65) Prior Publication Data
US 2015/0076359 A1    Mar. 19, 2015

Related U.S. Application Data

(60) Provisional application No. 61/857,231, filed on Jul. 22, 2013, provisional application No. 61/893,344, filed on Oct. 21, 2013.

(51) Int. Cl.
*G01J 1/42*    (2006.01)
*H05G 2/00*    (2006.01)
(Continued)

(52) U.S. Cl.
CPC ............... *H05G 2/008* (2013.01); *G01J 1/16* (2013.01); *G01N 21/956* (2013.01);
(Continued)

(58) Field of Classification Search
CPC .. H05G 2/008; G03F 7/70033; G03F 7/70266; B01J 2219/0894; G01J 1/16; G01N 2021/95676; G01N 21/15; G01N 21/956; G01N 2201/061
(Continued)

(56) References Cited

U.S. PATENT DOCUMENTS

| 7,087,914 B2 | 8/2006 | Akins et al. |
| 7,164,144 B2 | 1/2007 | Partlo et al. |

(Continued)

FOREIGN PATENT DOCUMENTS

EP    1376239 A2    1/2004

OTHER PUBLICATIONS

Author: Takayasu Mochizuki, Title: Laser plasma x-ray source by cryogenic target and high-rep rate slab YAG laser, Date:2000, Publisher: Proceedings of SPIE vol. 3886.*

(Continued)

*Primary Examiner* — David J Makiya
*Assistant Examiner* — Taeho Jo
(74) *Attorney, Agent, or Firm* — Suiter Swantz pc llo

(57) ABSTRACT

An EUV light source includes a rotatable, cylindrically-symmetric element having a surface coated with a plasma-forming target material, a drive laser source configured to generate one or more laser pulses sufficient to generate EUV light via formation of a plasma by excitation of the plasma-forming target material, a set of focusing optics configured to focus the one or more laser pulses onto the surface of the rotatable, cylindrically-symmetric element, a set of collection optics configured to receive EUV light emanated from the generated plasma and further configured to direct the illumination to an intermediate focal point, and a gas management system including a gas supply subsystem config- (Continued)

ured to supply plasma-forming target material to the surface of the rotatable, cylindrically-symmetric element.

25 Claims, 12 Drawing Sheets

(51) Int. Cl.
*G01J 1/16* (2006.01)
*G01N 21/956* (2006.01)
*G03F 7/20* (2006.01)

(52) U.S. Cl.
CPC ...... *G03F 7/70033* (2013.01); *G03F 7/70891* (2013.01); *G01N 2021/95676* (2013.01); *G01N 2201/061* (2013.01)

(58) Field of Classification Search
USPC .......................................................... 250/372
See application file for complete search history.

(56) References Cited

U.S. PATENT DOCUMENTS

| | | | |
|---|---|---|---|
| 7,317,196 B2 | 1/2008 | Partlo et al. | |
| 7,349,063 B2 | 3/2008 | Miyajima | |
| 8,057,053 B2 | 11/2011 | Hauf | |
| 8,480,243 B2 | 7/2013 | Bruchmann et al. | |
| 8,711,346 B2 | 4/2014 | Stokowski | |
| 8,785,082 B2 | 7/2014 | Xiong et al. | |
| 8,916,831 B2 | 12/2014 | Wang | |
| 8,963,110 B2 | 2/2015 | Hale et al. | |
| 2003/0219094 A1* | 11/2003 | Basting et al. | 378/34 |
| 2004/0108465 A1* | 6/2004 | Bakker et al. | 250/492.1 |
| 2005/0253160 A1 | 11/2005 | Strikovski et al. | |
| 2007/0285643 A1* | 12/2007 | Wedowski et al. | 355/67 |
| 2008/0032066 A1* | 2/2008 | Stiblert et al. | 427/595 |
| 2008/0197298 A1 | 8/2008 | Abe et al. | |
| 2009/0040511 A1 | 2/2009 | Wolters et al. | |
| 2009/0153975 A1* | 6/2009 | O'Reilly et al. | 359/626 |
| 2009/0224181 A1* | 9/2009 | Abe et al. | 250/504 R |
| 2009/0230326 A1 | 9/2009 | Vaschenko et al. | |
| 2010/0033704 A1 | 2/2010 | Shiraishi | |
| 2011/0140008 A1* | 6/2011 | Bergstedt et al. | 250/504 R |
| 2011/0141865 A1* | 6/2011 | Senekerimyan et al. | 369/47.15 |
| 2011/0204249 A1* | 8/2011 | Nagai et al. | 250/372 |
| 2012/0050704 A1* | 3/2012 | Levesque et al. | 355/53 |
| 2012/0050706 A1* | 3/2012 | Levesque et al. | 355/55 |
| 2012/0235049 A1 | 9/2012 | Wang | |
| 2012/0238096 A1 | 9/2012 | Xiong et al. | |
| 2013/0063803 A1* | 3/2013 | Delgado et al. | 359/278 |
| 2013/0119232 A1* | 5/2013 | Moriya et al. | 250/201.1 |
| 2013/0134318 A1* | 5/2013 | Abhari et al. | 250/372 |
| 2013/0322076 A1 | 12/2013 | Parker et al. | |
| 2014/0077099 A1* | 3/2014 | Hori et al. | 250/458.1 |
| 2014/0374611 A1 | 12/2014 | Hale et al. | |
| 2015/0055127 A1* | 2/2015 | De Jong et al. | 356/237.4 |

OTHER PUBLICATIONS

Anthony, Frank M. High Heat Load Optic: An Historical Overview, Optical Engineering, Feb. 1995, vol. 34, No. 2, 313-320.

* cited by examiner

SYSTEM AND METHOD FOR GENERATION OF EXTREME ULTRAVIOLET LIGHT

PRIORITY

The present application claims priority under 35 U.S.C. §119(e) to U.S. Provisional Patent Application Ser. No. 61/857,231, entitled EUV LIGHT SOURCE FOR LITHOGRAPHY MASK INSPECTION TOOLS, by Alexander Bykanov et al., filed Jul. 22, 2013, or is an application of which currently co-pending application(s) are entitled to the benefit of the filing date.

The present application further claims priority under 35 U.S.C. §119(e) to U.S. Provisional Patent Application Ser. No. 61/893,344, entitled CONTACTLESS THERMAL CONTROL OF MIRROR, by Layton Hale et al., filed Oct. 21, 2013, or is an application of which currently co-pending application(s) are entitled to the benefit of the filing date. The above-referenced provisional patent applications are hereby incorporated by reference in its entirety.

TECHNICAL FIELD

The present disclosure generally relates to the field of illumination systems and, more particularly, to plasma-based illumination systems.

BACKGROUND

As the demand for lithography-based device structures having ever-smaller features continues to increase, the need for improved illumination sources used for inspection of the associated reticles that lithographically print these ever-shrinking devices continues to grow. One such illumination source, utilized in lithographic systems, employs a laser produced plasma (LPP) generated via a metal target (e.g., Sn target) with a high power laser source (e.g., $CO_2$ laser). The use of EUV lights source currently utilized in lithographic systems are not adequate for use in EUV-based mask inspection systems. For example, EUV sources currently utilized in lithography systems have a power level that exceeds that necessary for EUV mask inspection, producing unneeded complexity and cost when implemented in an EUV mask inspection setting. Further, the use of metal targets in an EUV mask inspection system may lead to the generation of micro-particle and metal vapor debris, which, in turn, may contaminate the optics and vacuum environment of the given EUV mask inspection system. Therefore, it is desirable to provide a method and system that cure the defects of the prior art identified above.

SUMMARY

An apparatus for generating extreme ultra-violet (EUV) light is disclosed, in accordance with one illustrative embodiment of the present disclosure. In one embodiment, the apparatus includes a vacuum chamber. In another illustrative embodiment, the apparatus includes a rotatable, cylindrically-symmetric element having a surface at least partially coated with a plasma-forming target material and disposed within the vacuum chamber. In another illustrative embodiment, the apparatus includes a drive laser source configured to generate one or more laser pulses sufficient to generate EUV light via formation of a plasma by excitation of the plasma-forming target material. In another illustrative embodiment, the apparatus includes a set of focusing optics configured to focus the one or more laser pulses onto a portion of the surface of the rotatable, cylindrically-symmetric element. In another illustrative embodiment, the apparatus includes a set of collection optics configured to receive EUV light emanated from the plasma generated in response to the excitation of the plasma-forming target material and further configured to direct the illumination to an intermediate focal point. In another illustrative embodiment, the apparatus includes a gas management system including a gas supply subsystem configured to supply plasma-forming target material to the surface of the rotatable, cylindrically-symmetric element.

An inspection system is disclosed, in accordance with one illustrative embodiment of the present disclosure. In one illustrative embodiment, the inspection system includes an illumination sub-system including: a vacuum chamber; a rotatable, cylindrically-symmetric element having a surface at least partially coated with a plasma-forming target material and disposed within the vacuum chamber; a drive laser source configured to generate one or more laser pulses sufficient to generate EUV light via formation of a plasma by excitation of the plasma-forming target material; a set of focusing optics configured to focus the one or more laser pulses onto a portion of the surface of the rotatable, cylindrically-symmetric element; a set of collection optics configured to receive EUV light emanated from the plasma generated in response to the excitation of the plasma-forming target material and further configured to direct the illumination to an intermediate focal point; and a gas management system including a gas supply subsystem configured to supply plasma-forming target material to the surface of the rotatable, cylindrically-symmetric element. In another illustrative embodiment, the inspection system includes a set of illuminator optics configured to direct illumination from the one or more collection optical elements to one or more specimens. In another illustrative embodiment, the inspection system includes a detector. In another illustrative embodiment, the inspection system includes a set of projection optics configured to receive illumination from the surface of the one or more specimens and direct the illumination from the one or more specimens to the detector.

A lithography system is disclosed, in accordance with one illustrative embodiment of the present disclosure. In one illustrative embodiment, the lithography system includes an illumination sub-system including: a vacuum chamber; a rotatable, cylindrically-symmetric element having a surface at least partially coated with a plasma-forming target material and disposed within the vacuum chamber; a drive laser source configured to generate one or more laser pulses sufficient to generate EUV light via formation of a plasma by excitation of the plasma-forming target material; a set of focusing optics configured to focus the one or more laser pulses onto a portion of the surface of the rotatable, cylindrically-symmetric element; a set of collection optics configured to receive EUV light emanated from the plasma generated in response to the excitation of the plasma-forming target material and further configured to direct the illumination to an intermediate focal point; and a gas management system including a gas supply subsystem configured to supply plasma-forming target material to the surface of the rotatable, cylindrically-symmetric element; and a set of illuminator optics configured to direct collected illumination to a mask; and a set of projection optics configured to receive illumination reflected from the mask and direct the reflected illumination from the mask to one or more wafers.

A cooled mirror apparatus is disclosed, in accordance with one illustrative embodiment of the present disclosure. In one illustrative embodiment, the cooled mirror apparatus includes a mirror assembly including a mirror positioned on a first side of the mirror assembly and a first plurality of heat transfer elements formed in a first pattern positioned on a second side of the mirror assembly opposite the first side. In another illustrative embodiment, the cooled mirror apparatus includes a temperature control assembly including a second plurality of heat transfer elements formed in a second pattern compatible with the first pattern. In another illustrative embodiment, the temperature control assembly is positioned relative to the mirror assembly in order to interleave the first plurality of heat transfer elements with the second plurality of heat transfer elements. In another illustrative embodiment, the second plurality of heat transfer elements are offset from the first plurality of heat transfer elements by a selected offset distance. In another illustrative embodiment, the first plurality of heat transfer elements is configured to transfer heat to the second plurality of heat transfer elements via at least one of radiation and gas conduction.

An inspection system is disclosed, in accordance with one illustrative embodiment of the present disclosure. In one illustrative embodiment, the inspection system includes an illumination sub-system including a set of collection optics including one or more mirrors configured to collect illumination from an illumination source. In another illustrative embodiment, the inspection system includes a set of illuminator optics including one or more mirrors configured to direct illumination from the one or more mirrors of the collection optics to one or more specimens. In another illustrative embodiment, the inspection system includes a detector. In another illustrative embodiment, the inspection system includes a set of projection optics including one or more mirrors configured to receive illumination from the surface of the one or more specimens and direct the illumination from the one or more specimens to the detector. In another illustrative embodiment, at least one of the one or more mirrors of the set of collection optics, the one or more mirrors of the set of illuminator optics and the one or more mirrors of the set of projection optics includes a cooled mirror device. In one illustrative embodiment, the cooled mirror device includes a mirror assembly including a mirror positioned on a first side of the mirror assembly and a first plurality of heat transfer elements formed in a first pattern positioned on a second side of the mirror assembly opposite the first side; and a temperature control assembly including a second plurality of heat transfer elements formed in a second pattern compatible with the first pattern, the temperature control assembly positioned relative to the mirror assembly in order to interleave the first plurality of heat transfer elements with the second plurality of heat transfer elements, the second plurality of heat transfer elements offset from the first plurality of heat transfer elements by a selected offset distance, wherein the first plurality of heat transfer elements are configured to transfer heat to the second plurality of heat transfer elements via at least one of radiation and gas conduction.

A lithography system is disclosed, in accordance with one illustrative embodiment of the present disclosure. In one illustrative embodiment, the lithography system includes an illumination sub-system including a set of collection optics including one or more mirrors configured to collect illumination from an illumination source. In another illustrative embodiment, the lithography system includes a set of illuminator optics including one or more mirrors direct collected illumination to a mask. In another illustrative embodiment, the lithography system includes a set of projection optics including one or more mirrors receive illumination reflected from the mask and direct the reflected illumination from the mask to one or more wafers. In another illustrative embodiment, at least one of the one or more mirrors of the set of collection optics, the one or more mirrors of the set of illuminator optics and the one or more mirrors of the set of projection optics includes a cooled mirror device. In another illustrative embodiment, the cooled mirror device includes a mirror assembly including a mirror positioned on a first side of the mirror assembly and a first plurality of heat transfer elements formed in a first pattern positioned on a second side of the mirror assembly opposite the first side; and a temperature control assembly including a second plurality of heat transfer elements formed in a second pattern compatible with the first pattern, the temperature control assembly positioned relative to the mirror assembly in order to interleave the first plurality of heat transfer elements with the second plurality of heat transfer elements, the second plurality of heat transfer elements offset from the first plurality of heat transfer elements by a selected offset distance, wherein the first plurality of heat transfer elements are configured to transfer heat to the second plurality of heat transfer elements via at least one of radiation and gas conduction.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

FIGS. 1 through 7 generally illustrate embodiments of a system and method for generating extreme ultraviolet (EUV) light, in accordance with one or more embodiments of the present invention.

Embodiments of the present disclosure are directed to the exposure of a rotating cylindrically-symmetric element (e.g., cylinder) to one or more laser pulses from a drive laser source (e.g., drive laser) to generate an EUV light output. In the case of plasma-based illumination (e.g., EUV light), the cylindrically-symmetric element provides a stable, uniform solid plasma-forming material surface (e.g., xenon surface). Additional embodiments of the present disclosure provide for a mask inspection system, a wafer inspection system or a lithography system (or other optical system) incorporating the plasma-based rotating cylinder source described herein.

EUV light sources designed for lithography tools typically have high average power (e.g., 100 W and above) at 2% bandwidth with a central wavelength of 13.5 nm. Such systems typically employ a laser produced plasma (LPP) with a metal target (e.g., Sn) and a high power laser (e.g., $CO_2$ with wavelength of 10.6 μm). Such a combination is well suited for achieving high conversion efficiency (up to 4-5% in band) and high average power (about 100 W and above).

The use of such a lithography-based light source for inspection purposes leads to a redundant power level resulting in high complexity and cost. Further, the use of metal targets results in generation of debris in the form of microparticles and metal vapor, which may contaminate the optics and vacuum chamber.

Some embodiments of the present invention are directed to EUV mask inspection systems that do not generally demand high power. Rather, brightness is typically a larger concern in the context of EUV-based mask inspection. In this regard, the present invention, when used in the context of EUV mask inspection system, may display moderate average power (e.g., below 10 W), while possessing a small source size, which results in high brightness (e.g., above 10 $W/mm^2$ sr). Further, the small EUV source size of the mask inspection system(s) of the present disclosure may be achieved by tight focusing of the drive laser (e.g., to a spot less than 50-100 μm in diameter).

Figure 1:
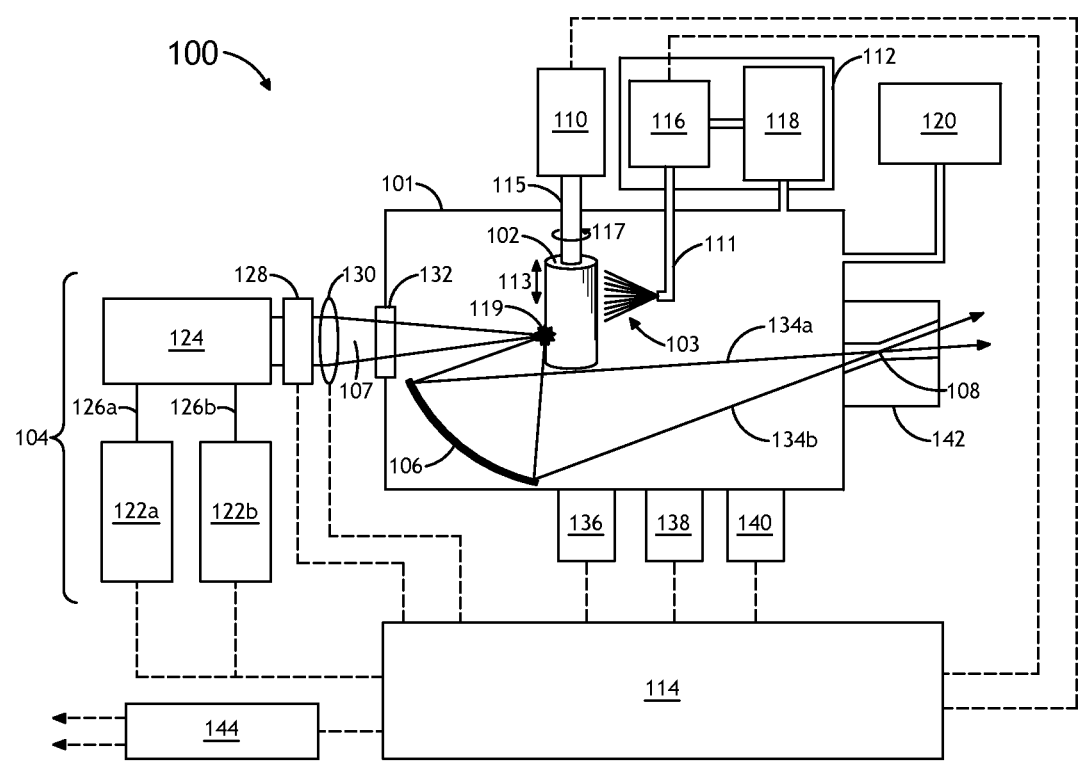
FIG. 1 is a block diagram illustrating an EUV light source, in accordance with an embodiment of this disclosure.

FIG. 1 illustrates a block diagram view of an EUV light source 100, in accordance with one or more embodiments of the present disclosure. In one embodiment, the system 100 includes a rotatable, cylindrically-symmetric element 102 having a surface at least partially coated with a plasma-forming target material and disposed within a vacuum chamber 101. In another embodiment, the system 100 includes a drive laser source 104 configured to generate one or more laser pulses sufficient to generate EUV light via formation of a plasma by excitation of the plasma-forming target material on the rotatable, cylindrically symmetric element 102. In another embodiment, the system 100 includes a gas management system 112 including a gas supply subsystem 116 configured to supply plasma-forming target material 103 to the surface of the rotatable, cylindrically-symmetric element 102. In another embodiment, the system 100 includes one or more control systems 114 configured to control one or more functions of one or more subsystems of system 100.

In one embodiment, the drive laser source 104 is suitable for initiating and/or maintaining a plasma in the material 103 once deposited on the surface of the rotatable, cylindrically-symmetric element 102. In this regard, the drive laser source 104 may supply the energy required to rapidly heat the plasma-forming target material to a plasma, which, in turn, emits EUV light.

In one embodiment, the drive laser source 104 may include, but is not limited to, one or more drive lasers. The number and type of lasers used in the drive laser source 104 may depend on a number of factors including, but not limited to, the required power output of the individual lasers, the desired EUV light power output, and the efficiency of the EUV light generation process. As an example, EUV light is used by photolithography mask inspection systems, but such systems do not require the high EUV light power output of primary photolithography systems. An EUV mask inspection system may only require EUV light in the range of 10 W, but with high brightness in a small area. In the case of mask inspection systems, total laser output in the range of a few kilowatts is needed, with the output being focused onto a small target spot (e.g., less than 100 μm in diameter).

The drive source 104 may include any pulsed or modulated illumination source known in the art. For example, the drive laser source 104 may include, but is not limited to, a pulsed laser. In one embodiment, the drive laser source 104 may include, but is not limited to, one or more solid state lasers. For example, the drive laser source 104 may include, but is not limited to, one or more Nd:YAG, Er:YAG, Yb:YAG, Ti:Sapphire, Nd:Vanadate, and like lasers. In another embodiment, the drive laser source 104 may include, but is not limited to, a gas-discharge laser. For example, the drive laser source 104 may include, but is not limited to, one or more excimer lasers. In another embodiment, the drive laser source 104 may include, but is not limited to, any laser system capable of emitting light having a wavelength less than 1 μm.

In another embodiment, the drive laser source 104 includes two or more lasers. For example, as shown in FIG. 1, the drive laser source 104 may include a first laser 122a and a second laser 122b. In another embodiment, the first laser 122a emits radiation 126a and the second laser 122b emits radiation 126b.

In another embodiment, the radiation 126a and 126b is combined into a combined beam 107 via beam combiner 124. In another embodiment, the beam combiner 124 further provides beam conditioning, such as beam expansion or collimation.

In another embodiment, system 100 includes a beam diagnostic tool 128. For example, the beam diagnostic tool 128 may be positioned to receive the output from the beam combiner 124. In this regard, the combined beam 107 is emitted by beam combiner 124 through beam diagnostic tool 128. In one embodiment, beam diagnostic tool 128 measures and/or monitors one or more characteristics of the one or more laser pulses of the beam 107 generated by the drive laser source 104. In this regard, the beam diagnostics tool 128 may acquire information about the beam 107, such as direction, temporal characteristics, and quality of the beam. In another embodiment, the beam diagnostics tool 128 is communicatively coupled to control system 114. In this regard, the beam diagnostics tool 128 may transmit the acquired beam information to the control system 114. In one embodiment, the control system 114 may receive the one or more monitored parameters from the beam diagnostic subsystem 128 and then adjust one or more parameters of system 100 in response to the monitor beam parameters. For example, the control system 114 may adjust one or more parameters of the drive laser source 104, one or more parameters of the rotatable, cylindrically-symmetric element 102, one or more parameters of the vacuum chamber 101, one or more parameters of the set of focusing optics or collection optics and one or more parameters of the gas supply subsystem. In another embodiment, the control system 114 may store the measured information acquired with the beam diagnostics tool 128 in memory and/or used for safety monitoring of the system 100 and the various subsystems (e.g., drive laser source 104).

In another embodiment, the EUV source 100 includes a set of focusing optics 130. In one embodiment, the one or more focusing optics configured to actively focus the one or more laser pulses from the drive laser source onto a plasma generation region of the rotatable, cylindrically-symmetric element. In one embodiment, control system 114 is communicatively coupled to the one or more focusing optics and configured to adjust the focus of the one or more laser pulses from the drive laser source 104. For example, control system 114 may adjust the focus of the one or more laser pulses from the drive laser source 104 in response to various monitored parameters (e.g., characteristic of beam 107, characteristic of EUV light, position of laser beam 107 relative to cylinder 107, tilt of cylinder 102 and the like) received by the control system 114.

For example, the laser beam 107 may be focused to the focal spot with optics 130, which can be adjusted (e.g., adjusted in X, Y and Z directions and tilt) with translational and/or rotational stages controlled by control system 114. Further, the EUV source 100 may provide focusing of the laser beam 107 to a spot with diameter less than 100 µm with a medium NA lens 130, providing a means for protecting the optics, while maintaining a fairly small diameter for the EUV collector in the case of an axial collector. As such, the wavelength of the laser may be chosen to be approximately 1 µm or less in order to meet the above criteria of a diffraction-limited focal spot.

In another embodiment, the vacuum chamber 101 includes one or more vacuum windows 132. For example, the laser beam 107 passes through vacuum window 132, which may also serve as a focusing optical element. It is noted herein that the EUV source 100 may include several input windows for combining multiple beams from multiple lasers into same focal spot. In another embodiment, the input window 132 may be protected from energetic streams emitted by plasma 119 by a pellicle (not shown) installed inside the vacuum chamber on the laser beam path.

Figure 2A:
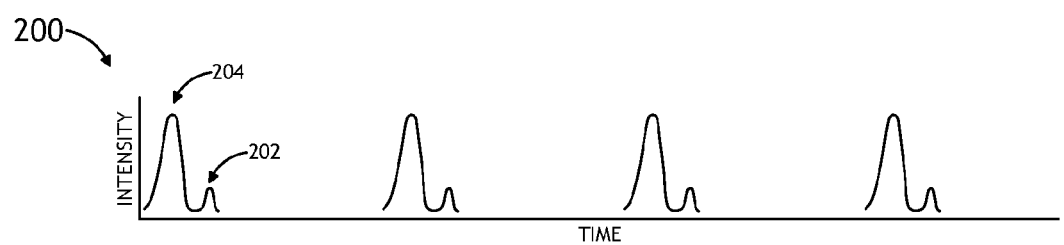
FIGS. 2A-2C are conceptual illustrations of a series of laser pulses including one or more pre-pulses and one or more main pulses, in accordance with an embodiment of this disclosure.
Figure 2B:
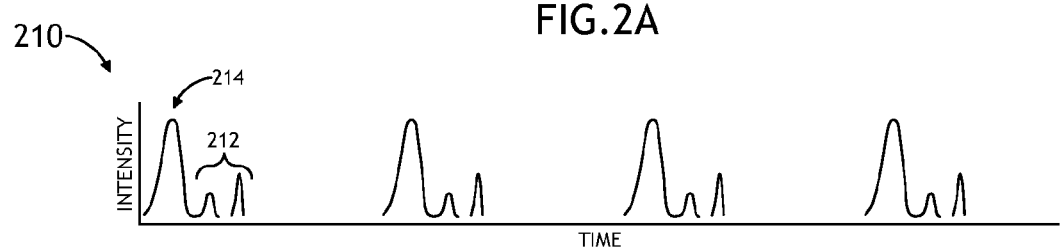
Figure 2C:
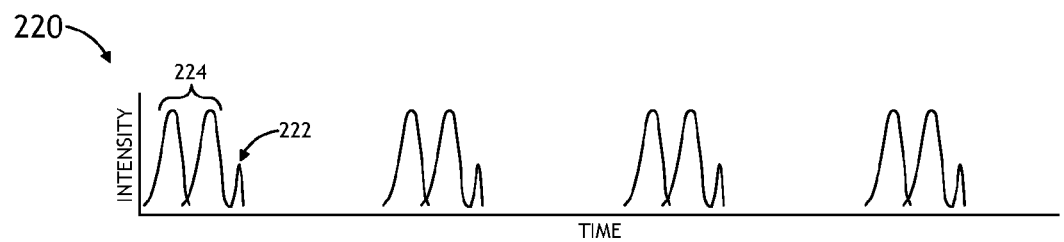

FIGS. 2A-2C illustrate a series of waveforms of the drive laser source 104, in accordance with one or more embodiments of the present disclosure. In one embodiment, the one or more laser pulses generated by the drive laser source 104 include a series of laser pulses sufficient to generate EUV light via excitation of a portion of the plasma-forming target material. For example, the series of laser pulses may include a series of non-equal laser pulses, with one or more low energy pulses followed by one or more high energy pulses. It is noted herein that varying the intensity within a single set of laser pulses provides control over the plasma generation process of system 100, where the parameters of the pulses, such as energy distribution between pulses, pulse durations, and delays may be adjusted for optimal (or at least adequate) performance of system 100. In one embodiment, as shown in FIGS. 2A-2C, the series of laser pulses includes one or more pre-pulses (e.g., 202, 212, 222) and one or more main pulses (e.g., 204, 214, 224) sufficient to generate EUV light via excitation of a portion of the plasma-forming target material. For example, the series of laser pulses includes one or more pre-pulses (e.g., 202, 212, 222) sufficient to non-thermally ablate a portion of the plasma-forming target material and one or more main pulses (e.g., 204, 214, 224) sufficient to generate EUV light via excitation of a portion of the non-thermally ablated portion of the plasma-forming target material. For the purposes of the present disclosure, the term "pre-pulse" means any pulse preceding a primary or "main pulse" and having an intensity smaller than the "main" pulse. For the purposes of the present disclosure, the term "main pulse" means the pulse having full intensity, which may be used to excite the plasma-forming material into an EUV light generating state.

In one embodiment, as shown in FIG. 2A, the waveform 200 includes a pre-pulse 202 and a main pulse 204. In this regard, the pre-pulse 202 has an intensity that is a fraction of the intensity of the main the main pulse 204. In another embodiment, as shown in FIG. 2B, the waveform 210 includes two pre-pulses 212 and a main pulse 214. In this regard, both pre-pulses 212 have an intensity that is a fraction of the intensity of the main pulse 214. In another embodiment, as shown in FIG. 2C, the waveform 220 includes a single pre-pulse 222 and two main pulse 224. In this regard, the pre-pulse 222 has an intensity that is a fraction of the intensities of the main pulses 224.

In one embodiment, the one or more laser pulses of beam 107 may include a train of pulses with duration in the range of 5 to 50 ns. In another embodiment, the total average power of the beam 107 outputted by the drive laser source 104 may be in the range of 1-10 kW. In another embodiment, the combination of multiple laser outputs may include triggering multiple lasers synchronously. This may be accomplished by using multiple lasers having the same repetition rate or via sequential triggering, whereby multiple lasers are triggered one by one with equally spaced intervals. In one embodiment, the total repetition rate of the lasers pulses of the drive laser source 104 (after combination of multiple lasers) may be in the range of 1-50 kHz.

By way of example, a pre-pulse may have a duration that is less than 1 ns, resulting in a minimal amount of material ablated from the target and exposed to the main pulse, as required for EUV generation. For instance, one or more pre-pulse laser pulses may be delivered in form of a ps or fs laser pulse to facilitate non-thermal ablation of Xe disposed on the surface of the rotatable, cylindrically symmetric element 102. In this regard, the pre-pulse(s) provide for the minimization of thermal load on the Xe ice layer and thus minimize Xe evaporation, which reduces brightness of the Xe plasma due to re-absorption of the emitted EUV radiation by the Xe gas evaporated or sublimated from the rotatable, cylindrically symmetric element 102.

Referring again to FIG. 1, in one embodiment, the rotatable, cylindrically-symmetric element 102 is suitable for rotation about an axis. In one embodiment, the rotatable, cylindrically-symmetric element 102 includes a cylinder, as shown in FIG. 1. In other embodiments, the rotatable, cylindrically-symmetric element 102 includes any cylindrically symmetric shape in the art. For example, the rotatable, cylindrically-symmetric element 102 may include, but is not limited to, a cylinder, a cone, a sphere, an ellipsoid and the like. Further, the cylindrically-symmetric element 102 may include a composite shape consisting of two or more shapes. It is noted herein that for the purposes of descriptive convenience the system 100 and related embodiments are described in the context of a rotatable or rotating cylinder 102, as depicted in FIG. 1, however this should not be interpreted as a limitation on the present invention.

In another embodiment, the rotatable cylinder 102 is at least partially coated with a plasma-forming target material 103. The plasma-forming target material 103 may include any material known in the art that generates plasma when excited by an illumination source. For example, the target material 103 may include, but is not limited to, xenon. In another embodiment, the target material 103 may include a solid material disposed on the surface of the rotatable cylinder 102. For example, the target material 103 may include, but is not limited to, xenon frozen onto the surface of the rotatable cylinder 102.

In one embodiment, vacuum chamber 101 is a low pressure container in which the plasma that serves as the EUV light source is generated and the resulting EUV light is collected and focused. EUV light is strongly absorbed by gases, thus, reducing the pressure within vacuum chamber 101 serves to reduce the attenuation of the EUV light within the light source In one embodiment, the gas supply subsystem 116 of the gas management system 112 may supply a selected material 103 to the surface of the rotatable cylinder 102 within the vacuum chamber 101. For example, the gas supply subsystem 116 may supply a selected material 103 to the surface of the rotatable cylinder 102 via nozzle 111. In one embodiment, the gas supply subsystem 116 may direct a gas, liquid stream or spray onto the surface of the cylinder 102 as it rotates, and is maintained at a temperature below the freezing point of the selected material. For example, the selected material may include, but is not limited to, xenon and like materials. For instance, the rotatable cylinder 102 may be cooled below the xenon freezing point (e.g., −111.8° C.). Then, xenon may be applied to the surface of the rotatable cylinder 102 causing the xenon to freeze onto the surface of the rotatable cylinder 102 as it is rotated, thereby forming a solid xenon layer on the outer surface of the cylinder 102. In one embodiment, the rotatable cylinder 102 may include an internal reservoir for containing a coolant material. For example, in the case of xenon, the rotatable cylinder 102 may include an internal reservoir holding a volume of liquid nitrogen used to cool the applied xenon below the freezing point for xenon.

In another embodiment, the system 100 may include a mechanism used to improve the quality of the layer of plasma-forming material on the cylinder 102. In one embodiment, the system 100 may include a thermal device and/or a mechanical device located outside of the cylinder 102 suited to aid in forming (or maintaining) a uniform layer of the plasma-forming material on the surface of the cylinder 102. For example, in the case of xenon, the system 100 may include, but is not limited to, a heating element arranged to smooth or control the density of the xenon ice layer formed on the surface of the cylinder 102. By way of another example, in the case of xenon, the system 100 may include, but is not limited to, a blade device arranged to smooth and/or control the density of the xenon ice layer formed on the surface of the cylinder 102.

In another embodiment, the gas supply subsystem 116 may also serve to 'recoat' one or more portions of the cylinder 102 following exposure to the beam 107 from the drive laser source 104.

In another embodiment, the gas supply system 116 supplies one or more buffer gases to the vacuum chamber 101. For example, the gas supply system 116 may supply any buffer gas known in the art to vacuum chamber, such as, but not limited to, hydrogen, helium, argon, or other inert gases. The buffer gas also serves to protect the dynamic gas lock function of internal focus module 142.

In another embodiment, the gas management system 112 includes a plasma-forming material recycling subsystem 118. In one embodiment, the material recycling system 118 recovers the plasma-forming material (e.g., xenon) from vacuum chamber 101 and resupplies it to gas supply system 116.

In another embodiment, the vacuum chamber 101 includes a vacuum system 120 suitable for establishing and maintaining the low-pressure environment of vacuum chamber 101. For example, the vacuum system 120 may include one or more vacuum pumps, such as, but not limited to, a turbo pump and/or a roots pump backed with a dry pumping unit and equipped with an exhaust system (not shown) for safe utilization of volatile gases, such as $H_2$.

In another embodiment, the system 100 includes at least one actuation device 110. In one embodiment, the actuation device 110 is configured to actuate the rotatable cylinder 102. In one embodiment, the actuation device 110 is configured to control the axial position of the rotatable cylinder 102. For example, the actuation device 110 includes a linear actuator (e.g., linear translation stage) configured to translate the rotatable cylinder 102 along an axial direction 113 relative to the beam 107 from the drive laser source 104. In another embodiment, the actuation device 110 is configured to control the rotational state of the rotatable cylinder 102. For example, the actuation device 110 may include a rotational actuator (e.g., rotational stage) configured to rotate the rotatable cylinder 102 along rotational direction 117 such that the beam 107 traverses along the surface of the cylinder 102 at a selected axial position at a selected rotational speed. In another embodiment, the actuation device 110 is configured to control the tilt of the rotatable cylinder 102. For example, a titling mechanism of the actuation device 110 may be used to adjust the tilt of the cylinder 102 in order to align the plasma position 119 with the primary focus of the collection optics 106.

In another embodiment, the rotatable cylinder 102 may be coupled to the actuation device 110 via shaft 115. It is recognized herein that the present invention is not limited to the actuation device 110, as described previously herein. As such, the description provided above should be interpreted merely as illustrative. For instance, the drive source 104 may be disposed on an actuating stage (not shown), which provides translation of the beam 107 relative to the cylinder 102. In another instance, the beam 107 may be controlled by various optical elements to cause the beam to traverse surface of the cylinder 102 as desired. It is further recognized that any combination of cylinder 102, source 104 and beam 107 control may be used to traverse the beam 107 across the cylinder 102 as required by the present invention.

In another embodiment, the actuation device 110 and/or the drive laser source 104 are communicatively coupled to the control system 114. In one embodiment, the control system 114 controls the actuation of the rotatable cylinder 102 along an axial direction 113 relative to the drive laser source 104. In another embodiment, the control system 114 controls the drive laser source 104 (e.g., pulse timing, direction and etc.). In this regard, the control system 114 may direct the actuation device 110 and the cylinder 102 to trace the pulsed illumination 107 across the surface of the cylinder, as the cylinder rotates, in any manner described in the present disclosure.

Figure 3:
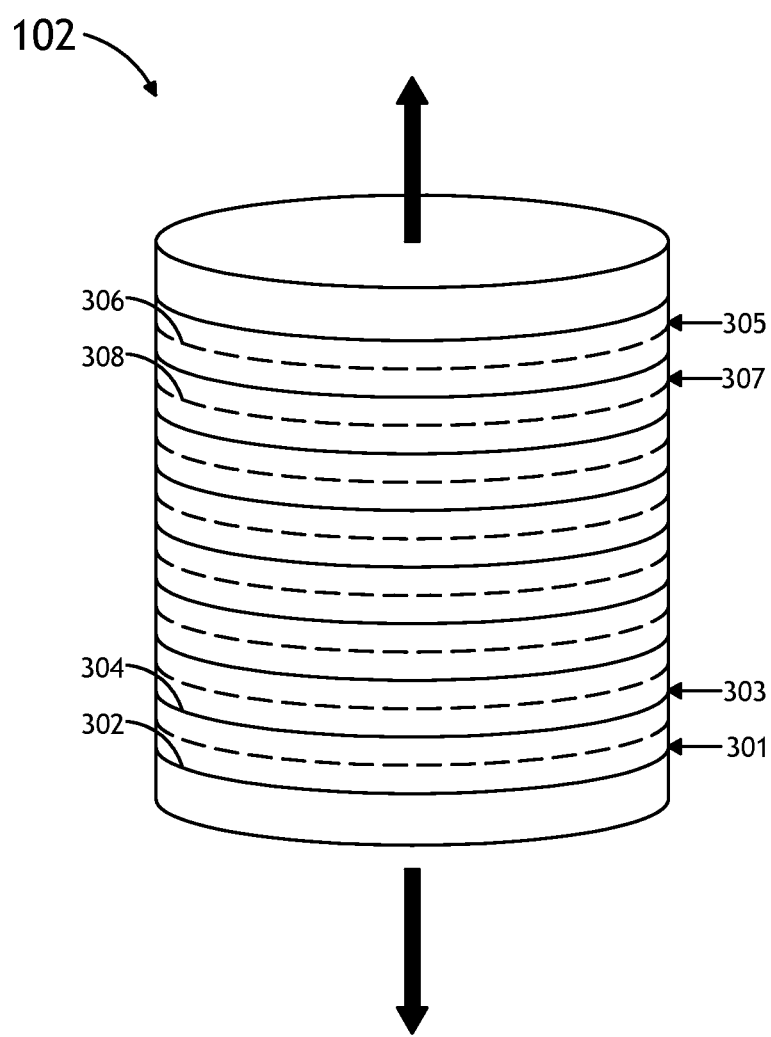
FIG. 3 is a block diagram illustrating a pulsed axial translation scheme, in accordance with an embodiment of this disclosure.

FIG. 3 illustrates a conceptual view of the traced paths associated with a pulsed translation process, in accordance with one embodiment of the present disclosure. In one embodiment, the control system 114 may direct the actuation device 110 to repeatedly axially actuate the rotating cylinder 102 relative to the drive laser source 104 so to perform a pulsed axial translation process. In this regard, the control system 114 may direct the actuation device 110 to align the drive laser source 104 at a first axial position 301 of the rotatable, cylindrically-symmetric element 102. Then, the actuation device 110 may rotate the rotatable, cylindrically-symmetric element to cause the beam 107 (including one or more laser pulses) of the drive laser source 104 to traverse the circumference of the rotatable, cylindrically-symmetric element 102 along the first axial position 301. The path traced by the drive laser source 104 at the first axial position 301 is depicted by the solid line 302. Then, the control system 114 may direct the actuation device 110 to axially translate the rotatable, cylindrically-symmetric element 102 relative to the drive laser source to align the drive laser source at a second axial position 303 of the rotatable, cylindrically-symmetric element 102. In turn, the actuation device 110 may rotate the rotatable, cylindrically-symmetric element 102 to cause the beam 107 of the drive laser source to traverse the circumference of the rotatable, cylindrically-symmetric element 102 along the second axial position 303. The path traced by the drive laser source 104 at the second axial position 303 is depicted by the solid line 304. In this regard, the control system 114 may direct the actuation device 110 to carry out a series of N pulsed translations, allowing the beam 107 to traverse the circumference of rotatable, cylindrically-symmetric element 102 at each of the N axial positions.

In another embodiment, the pulsed translation process may include aligning the beam 107 at a series of axial positions (e.g., 301, 303 and so on) during a "downward stroke" of the rotatable, cylindrically-symmetric element 102, depicted by the downward facing arrow in FIG. 3. For example, as shown in FIG. 3, the solid lines represent the beam paths 107 at each of the N axial positions formed by the "downward" pulsed axial translation of the element 102 relative to the beam 107 (not shown in FIG. 3).

In another embodiment, the pulsed translation process may include aligning the beam 107 at a series of axial positions (e.g., 305 and 307) during an "upward stroke" of the rotatable, cylindrically-symmetric element 102, depicted by the upward arrow in FIG. 3. For example, as shown in FIG. 3, the dotted lines (e.g., 306 and 308) represent the paths traced by the beam 107 at each of the M axial positions formed by the "upward" pulsed axial translation of the element 102 relative to the beam 107.

In another embodiment, the control system 114 may direct the actuation device 110 to offset the axial positions of the downward stroke of rotatable, cylindrically-symmetric element 102 relative to the axial positions of the upward stroke rotatable, cylindrically-symmetric element 102. In this regard, the beam 107 traces performed during the downward stroke of the rotatable, cylindrically-symmetric element 102 are interlaced with the beam 107 traces performed during the upward stroke of rotatable, cylindrically-symmetric element 102, as depicted in FIG. 3. For the purposes of descriptive convenience, traces (e.g., 302, 304 and so on) for a single downward stroke (downward arrow) and traces (e.g., 306, 308 and so on) for single upward stroke (upward arrow) are depicted in FIG. 3. It is noted herein that the present invention is not limited to a single downward stroke and a single upward stroke. It is recognized herein that any number of upward and downward strokes may be implemented by source 104 by the repeated reversal between downward and upward axial translation via actuation device 110. Further, it is recognized herein that the axial positions associated with each stroke (downward or upward) of a series of strokes may be offset such that each trace of beam 107 along the surface of the rotatable, cylindrically-symmetric element 102 traverses "new" or "fresh" plasma-forming material. In this regard, the traces associated with an upward stroke (e.g., 306, 308 and so on) may be interlaced with respect to the traces associated with a downward stroke (e.g., 302, 304 and so on), as depicted, but not limited to, by the interlaced dotted and solid lines traversing the surface of cylinder 102 of FIG. 3.

It is recognized herein that the pulsed axial translation scheme described herein may provide a more uniform EUV emission replenishment of the plasma-forming material layer (e.g., solid Xe layer) across the entire surface of the rotatable, cylindrically-symmetric element 102. By way of example, the axial speed of the rotatable, cylindrically-symmetric element 102 during a translation pulse is in the range of 1 m/s to 50 m/s (e.g., 10 m/s). Further, the pulse translation rate is correlated with the rotational speed of the rotatable, cylindrically-symmetric element 102 (e.g., less than 20 Hz).

In another embodiment, the control system 114 may direct the actuation device 110 to axially actuate the rotating cooled cylinder 102 relative to the drive laser source 104 so to cause the beam 107 of the drive laser source 104 to trace out a helical pattern on the surface of the rotatable, cylindrically-symmetric element 102 in a continuous or near-continuous translation process. A continuous translation process is described in U.S. patent application Ser. No. 14/309,393 to Hale et al., filed on Jun. 19, 2014, which is incorporated herein by reference in the entirety.

In another embodiment, the gas supply subsystem 116 is configured to recoat portions of the rotatable cylinder with the plasma-forming material 103. In one embodiment, the gas supply subsystem 116 is configured to recoat previously-illuminated portions of the rotatable cylinder 102 with the plasma-forming material 103. For example, the gas supply subsystem 116 may recoat spots previously 'hit' with illumination 107 with a plasma-forming material, such as, but not limited to, xenon. Further, the length of the cylinder 102 and the axial speed of the cylinder 102 may be selected so as to provide ample time for the plasma-forming material (e.g., xenon) to solidify on the cylinder 102 before the next illumination exposure.

Figure 4A:
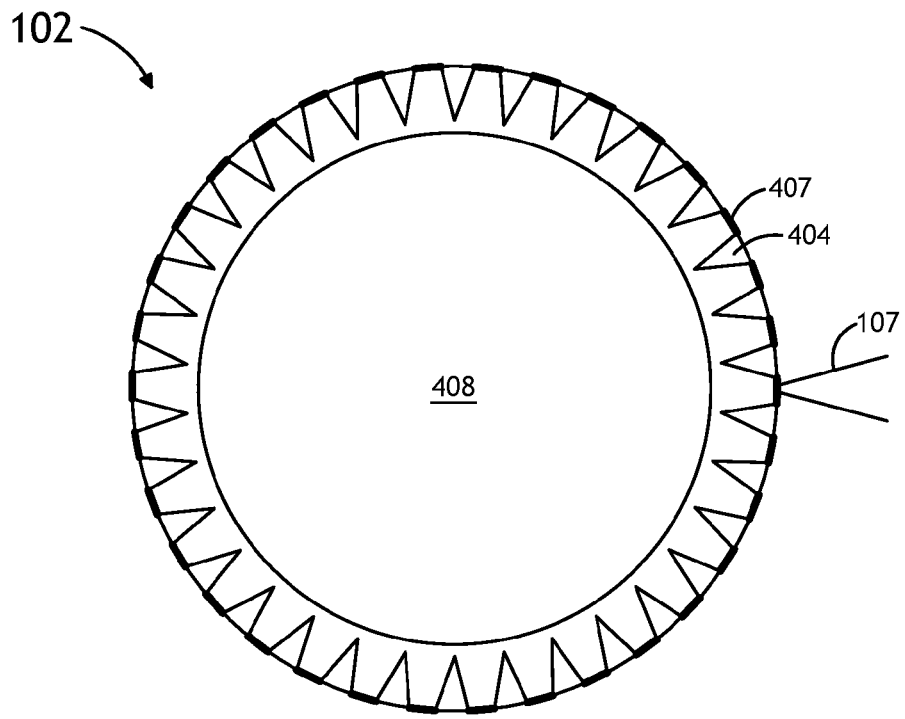
FIGS. 4A-4B are cross-sectional views of a rotatable cylinder equipped with a series of mass-limited plasma-forming targets, in accordance with an embodiment of this disclosure.
Figure 4B:
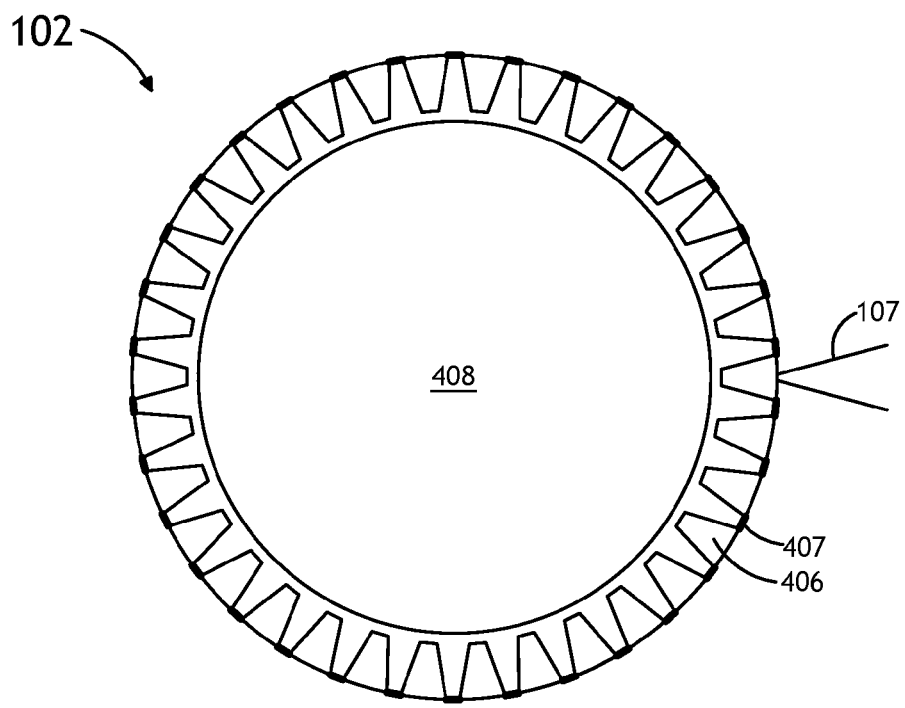

FIGS. 4A and 4B illustrate cross-sectional views of a rotatable, cylindrically-symmetric element 102 having mass-limited plasma-forming material targets, in accordance with one or more embodiments of the present invention. In one embodiment, as shown in FIGS. 4A and 4B, multiple mass-limited targets (e.g., 404 or 406) are embedded within the surface of the rotatable, cylindrically-symmetric element 102. In this regard, each mass-limited target is formed by the formation of the plasma-forming solid (e.g., Xe ice) within a "pit" in the surface of the rotatable, cylindrically-symmetric element 102. In another embodiment, rotatable, cylindrically-symmetric element 102 is filled with a cryogenic liquid 408 (e.g., liquid nitrogen) which serves to freeze the given plasma-forming material and maintain it in a frozen state.

In another embodiment, the mass-limited targets may be embedded within the surface of the rotatable, cylindrically-symmetric element 102 along one or more paths to be traced by beam 107. In this regard, the control system 114 may direct the actuation device 110 and/or drive laser source 104 such that the beam 107 moves from mass-limited target to mass-limited target along a given path or paths of the beam 107 across the surface of the rotatable, cylindrically-symmetric element 102 (e.g., helical path or paths defined by pulsed translation process).

It is recognized herein that the implementation of mass-limited targets disposed within the pits of the surface of the rotatable, cylindrically-symmetric element 102 may serve to provide a thermal barrier between adjacent mass-limited targets (e.g., Xe targets). As such, the use of mass-limited targets disposed within pits of the surface of the rotatable, cylindrically-symmetric element 102 may aid in reducing spot-to-spot heat-spreading, which commonly leads to excess vaporization of the plasma-forming material (e.g., formation of Xe gas in case of solid Xe layer).

In one embodiment, as shown in FIG. 4A, multiple cone-shaped mass-limited targets 404 are embedded within the surface of the rotatable, cylindrically-symmetric element 102. In another embodiment, as shown in FIG. 4B, multiple trapezoidal-shaped mass-limited targets 406 are embedded within the surface of the rotatable, cylindrically-symmetric element 102. It is noted herein that trapezoidal shaped mass-limited targets 406 as depicted in FIG. 4B thin-walled bottoms may promote bottom-to-top plug formation via freezing of the material (e.g., Xe) within the pits.

In another embodiment, although not shown, the mass-limited targets may consist of rings of plasma-forming material embedded within the surface of the rotatable, cylindrically-symmetric element 102 and spaced along the axial direction. It is noted herein that such a ring structure may provide for continuous EUV light generation during one rotation about the element 102, while also providing reduced plasma-forming material vaporization along the axial direction.

It is further noted herein that the present invention is not limited to cone- and trapezoidal-shaped mass-limited targets. It is recognized herein that the mass-limited targets may take on any geometrical shape (or a portion of a geometrical shape) known in the art, such as, but not limited to, a cone, a trapezoid, a pyramid, a cylinder, an ellipsoid, a sphere, a ring and the like.

In another embodiment, the surface of the rotatable, cylindrically-symmetric element 102 may be coated with high reflective coating 407 (e.g., high reflect IR coating) to minimize the thermal load on the rotatable, cylindrically-symmetric element 102. For instance, the reflective layer 407 may serve to reduce heating by non-plasma-forming portions of the rotatable, cylindrically-symmetric element 102 by beam 107. The reflective coating 407 may include, but is not limited to, a metal coating (e.g., Cu, Ag, Au, Mo, Pt, and the like) or multilayer dielectric coating. It is further recognized herein that special coatings with a high laser threshold may aid in preventing surface modification and/or ablation of the rotatable, cylindrically-symmetric element 102, thereby increasing system lifetime In another embodiment, as shown in FIGS. 4A and 4B, the mass-limited targets may be structured larger than the beam waist associated with beam 107.

Figure 5:
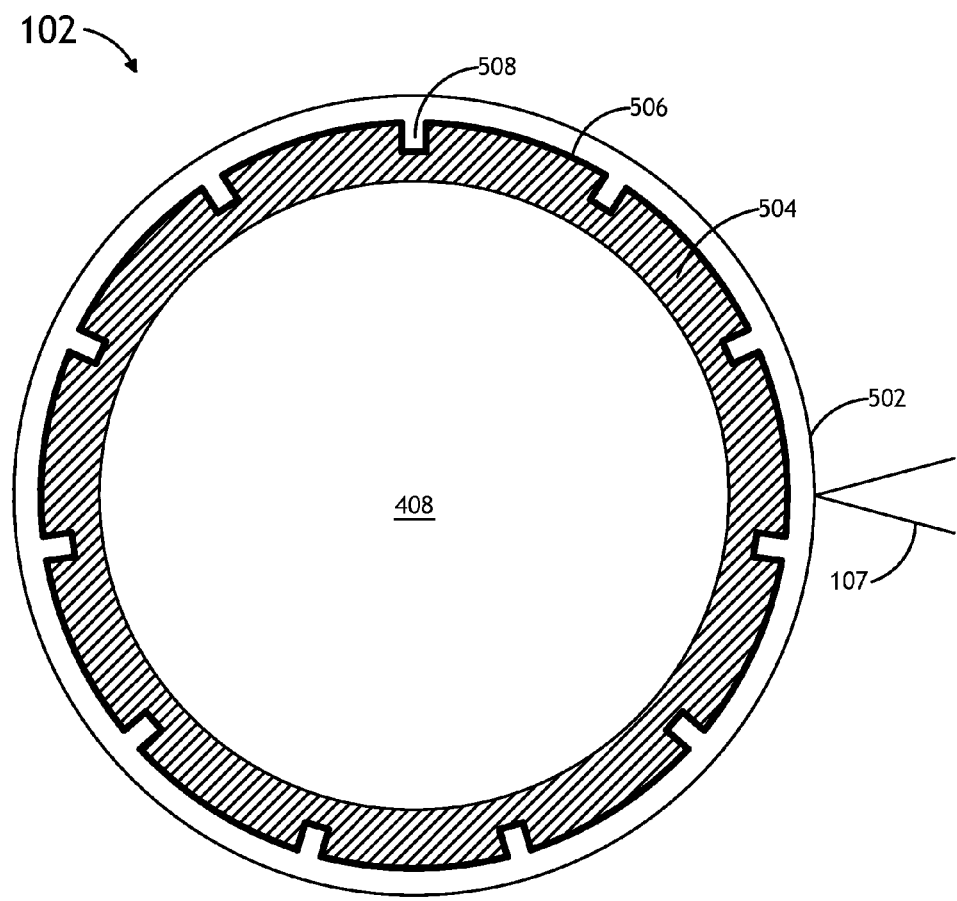
FIG. 5 is a cross-sectional view of a rotatable cylinder equipped with a series of adhesion structures, in accordance with an embodiment of this disclosure.

FIG. 5 illustrates a cross-sectional view of a rotatable, cylindrically-symmetric element 102 having a reflective surface, in accordance with one embodiment of the present invention. In one embodiment, the rotatable, cylindrically-symmetric element 102 has a metal wall 504 with high thermal conductivity (e.g., Cu wall) and a cryogenic temperature fluid 408 (e.g., liquid nitrogen) within the element 102 having a temperature below the triple point of given plasma-forming material. It is recognized herein that laser radiation 107 may partially penetrate the solid plasma-forming layer 502 (e.g., frozen Xe layer) causing degradation of the surface of the rotatable, cylindrically-symmetric element 102. It is further recognized herein that a highly reflective surface 506 may aid in preventing surface degradation of the cylindrically-symmetric element 102 by reflecting radiation that penetrates the plasma-forming layer 502, thereby increasing system lifetime.

In one embodiment, the highly reflective surface 506 is achieved via polishing the surface of the rotatable, cylindrically-symmetric element 102. For example, the rotatable, cylindrically-symmetric element 102 may be formed from a highly conductive material (e.g., Cu, Ag, Au, Mo, Pt and the like) and then polished to achieve a highly reflective surface.

In another embodiment, the highly reflective surface 506 is achieved by depositing a metallic layer onto the rotatable, cylindrically-symmetric element 102 and then polishing the surface of the deposited layer. For example, the layer may be formed from a metal, such as, but not limited to, Cu, Ag, Au, Mo, Pt and the like, and then polished to achieve a highly reflective surface.

In another embodiment, the highly reflective surface 506 is achieved by coating the rotatable, cylindrically-symmetric element 102 with a dielectric multilayer. For example, the dielectric coating may include a multilayer coating with refractive index matched to the refractive index of the plasma-forming layer 502.

It is recognized herein that the reflective surfaces and/or coatings described herein may be implemented in combination with any configuration of the rotatable, cylindrically-symmetric element 102 and are not limited to the configuration depicted in FIGS. 4A, 4B and 5.

In another embodiment, the rotatable, cylindrically-symmetric element 102 may be substantially transparent to the beam 107 from the drive laser source 104. For example, the rotatable, cylindrically-symmetric element 102 may be formed from a highly conductive, yet transparent material such as, but not limited to, sapphire (e.g., synthetic sapphire).

It is recognized herein that as radiation from the laser beam 107 is absorbed by the outer surface of a metal rotatable, cylindrically-symmetric element 102 at a given spot on the element 102 the spot may become damaged and eject a large number of highly energetic particles outward from the element 102. These particles may damage nearby optics. In addition, the cylindrically-symmetric element 102 itself receives damage that accumulates over time, eventually rendering the element 102 unusable. For example, in the case of a xenon plasma and a copper or stainless steel cylinder 102, the existing copper or stainless steel element may be exposed to the high-power pulsed laser beam 107. It is noted that a portion of that laser radiation 107 is absorbed by the xenon and generates a xenon plasma (as discussed throughout the present disclosure). However, some of the laser energy is transmitted through the xenon and is absorbed by the copper or stainless steel base material. As a result, the high intensity laser beam 107 may cause damage to the rotatable, cylindrically-symmetric element 102, which, in turn, may eject particles in the vacuum chamber 101. In addition, the heat absorbed by wall of the rotatable, cylindrically-symmetric element 102 may be transferred through the wall into internal cryogenic fluid (e.g., liquid nitrogen) within the rotatable, cylindrically-symmetric element 102.

It is recognized herein that the use of a rotatable, cylindrically-symmetric element 102 having a wall that is nominally transparent to the radiation 107 from the drive laser 104 allows for the light not used in producing plasma 119 to be transmitted through the wall of the rotatable, cylindrically-symmetric element 102 and absorbed directly by the cryogenic liquid (e.g., liquid nitrogen). As such, only the small amount of light which is not transmitted through the transparent wall may lead to potential damage of the wall.

In one embodiment, the rotatable, cylindrically-symmetric element 102 may include a sapphire cylinder. It is noted herein that sapphire is a hard crystalline material and will generally experience less damage for a given amount of absorbed energy than a metal. It is further noted that because a drive laser source 104 may be selected such that sapphire is generally transparent to the drive laser wavelength (e.g., 1 μm), little of the power is absorbed by the rotatable, cylindrically-symmetric element 102. In addition, because sapphire exhibits a high thermal conductivity at cryogenic temperatures (e.g., liquid nitrogen temperatures), any laser power that is absorbed by the sapphire wall is quickly transferred to the cryogenic fluid (e.g., see 408 in FIGS. 4A, 4B and 5) within the center of the rotatable, cylindrically-symmetric element 102.

In another embodiment, the sapphire-based rotatable, cylindrically-symmetric element may be connected to stainless steel end plates (not shown) on the top and bottom for mounting to other interfaces. In another embodiment, in order to accommodate the difference in thermal expansion between the sapphire (or like material) and the stainless steel (or like material) as the element 102 is cycled from room temperature to cryogenic temperatures (e.g., liquid nitrogen temperatures) and back, a thin flexible material (e.g., Kovar) transition sleeve (not shown) may be implemented. In another embodiment, in order to attach the flexible material sleeve to the sapphire, the ends of the sapphire are first metalized with a thin layer of material, such as, but not limited to, Molybdenum-Tungsten and like materials. In another embodiment, the flexible material ring may then be brazed to the metallized portion on both ends of the sapphire element. In another embodiment, after the brazing operation is complete, the stainless steel flanges are welded to the flexible material sleeve using at least one of a tungsten inert gas (TIG) process, an electron beam, or a laser.

It is recognized herein that the transparent rotatable, cylindrically-symmetric element 102 is not limited to sapphire. Any transparent crystalline material known in the art suitable for transmitting the utilized radiation and supporting plasma production may be used in the present invention.

For example, any material that has a reasonably high thermal conductivity while at the same time being transparent to the laser radiation 107 may be used to construct the rotatable, cylindrically-symmetric element 102. For example, the rotatable, cylindrically-symmetric element 102 be formed from diamond.

In another embodiment, the transparent material may include one or more dopant materials with the crystal structure of the transparent material. For example, in the case of a sapphire cylinder element 102, the sapphire may be grown with a variety of dopants within its crystal structure. For instance, these dopants may include, but are not limited to, chromium (creating ruby rather than sapphire), magnesium, yttrium, or vanadium. It is further noted herein that these dopants may act as tracer elements to determine if any of the aluminum oxide particles found during development tests are from the sapphire drum or are instead from one of the various bare aluminum surfaces that are found in the source 100. It is noted that since those bare aluminum surfaces tend to oxidize to some extent during their fabrication and installation, corresponding particles create tend to consist of aluminum oxide, which may be chemically identical to the aluminum oxide of which a sapphire cylinder is composed.

In another embodiment, also shown in FIG. 5, adhesion of the plasma-forming material 502 to the outer surface of the rotatable, cylindrically-symmetric element 102 is improved by the formation of multiple adhesion structures 508 in the wall 504 of the rotatable, cylindrically-symmetric element 102. For example, as shown in FIG. 5, the adhesion structures may include of cylindrically-shaped adhesion structures, or "dimples." It is recognized herein that the adhesion structures 508 may take on any geometrical shape (or portion of geometrical shape) known in the art, such as but not limited to, a cone, a trapezoid, a pyramid, a cylinder, an ellipsoid, a sphere, a ring and the like.

In another embodiment, the system 100 includes a set of collection optics 106 arranged to collect plasma-based illumination emanating from the plasma-formed regions on the cylinder 102. For example, after EUV light is generated by the plasma excited by the drive laser source 104, the light may then be collected by collector 106. For example, the collector 106 may include any collector known in the art. For instance, the collector 106 includes any collector known in the art compatible with EUV light. In another embodiment, the collection optics 106 may direct and/or focus illumination emanating from the rotatable, cylindrically-symmetric element 102 to one or more downstream optical elements. In another embodiment, the collection optics 106 may be configured to focus illumination emanating from the rotatable, cylindrically-symmetric element 102 to an intermediate focus 108, as shown in FIG. 1. It is noted herein that the set of collection optics 106 (sometimes referred to as a "collector") may include one or more mirrors arranged between the plasma 119 and the intermediate focal point 108.

In one embodiment, the plasma 119 is generated at a location corresponding to the focal point of the beam 107, which also corresponds with the first focal point of the collection optics 106. For example, the collection optics 106 may include an off-axis segment of a prolate spheroid having two focal points. In one embodiment, the collection optics 106 may include a high quality polished surface coated with a multilayer mirror (e.g., Mo/Si or NbC/Si) suitable for EUV reflection. In another embodiment, EUV radiation emitted from plasma 119 is reflected by the collection optics 106 (e.g., see extreme rays 134a and 134b) and focused to the second focal spot 108, or the "intermediate focus." It is noted herein that the use of an off-axis collector for the rotatable, cylindrically-symmetric element 102 provides minimal obscuration of the reflected beam by the rotatable, cylindrically-symmetric element 102. In turn, the plasma-forming material on the surface of the rotatable, cylindrically-symmetric element 102 experiences a reduction of thermal load, thereby reducing evaporation of the plasma-forming material, such as xenon.

In another embodiment, the collection optics 106 may include one or more cooled mirror devices (see cooled mirror device 800 in FIG. 8), described in greater detail further herein.

In another embodiment, the system 100 includes an interface (IF) module 142 suitable for providing separation between the EUV generation subsystems of system 100 and projection optics of an optical system (e.g., inspection system, metrology system and the like), described in greater detail further herein, implementing the system 100 as an EUV source. In this regard, the focusing of the EUV beam at focal point 108 may allow for arrangement of the interface 142 with projection optics of the given optical system, thereby providing protection from possible debris and contaminants generated by system 100.

In another embodiment, the EUV source 100 includes one or more EUV diagnostic tools 136, 138 and 140 configured to monitor one or more characteristics of the generated EUV light. In another embodiment, the one or more EUV diagnostic tools 136, 138 and 140 are communicatively coupled to control system 114. In this regard, the control system 114 may receive one or more monitored parameters from the EUV diagnostic tools 136, 138 and 140. In another embodiment, the control system 114 is further configured to adjust at least one of plasma 119 position on rotatable, cylindrically-symmetric element 102 in response to one or more monitored parameters from the EUV diagnostic tools 136, 138 and 140. For example, the control system 114 may adjust the position of the plasma 119 on rotatable, cylindrically-symmetric element 102 by controlling (via actuation device 110) the axial, rotation and/or tilt actuation state of the rotatable, cylindrically-symmetric element 102 relative to the laser beam 107. By way of another example, the control system 114 may adjust the position of the plasma 119 on rotatable, cylindrically-symmetric element 102 by controlling (e.g., steering) the beam position (via active optical elements 130) relative to the surface of the rotatable, cylindrically-symmetric element 102. In another embodiment, the control system 114 is further configured to adjust a power level of the drive laser source 104 in response to one or more monitored parameters from the EUV diagnostic tools 136, 138 and 140. In another embodiment, the control system 114 is further configured to adjust the primary focus of the collection optics 106 in response to one or more monitored parameters from the EUV diagnostic tools 136, 138 and 140.

In one embodiment, the one or more EUV diagnostic tools (e.g., tool 136) may include optical and/or EUV plasma imaging tools. In another embodiment, the one or more EUV diagnostic tools (e.g., tool 138) may include one or more EUV power meters for measurement of the EUV power emitted by the plasma 119. It is recognized herein that the source 100 may employ any diagnostic tool known in the art suitable for monitoring one or more parameters associated with plasma-based EUV light production. For example, the one or more EUV diagnostic tools (e.g., tool 140) may further include gas monitoring device (e.g., residual gas analyzer), temperature monitor, pressure monitor and/or radiation monitor.

Figure 6:
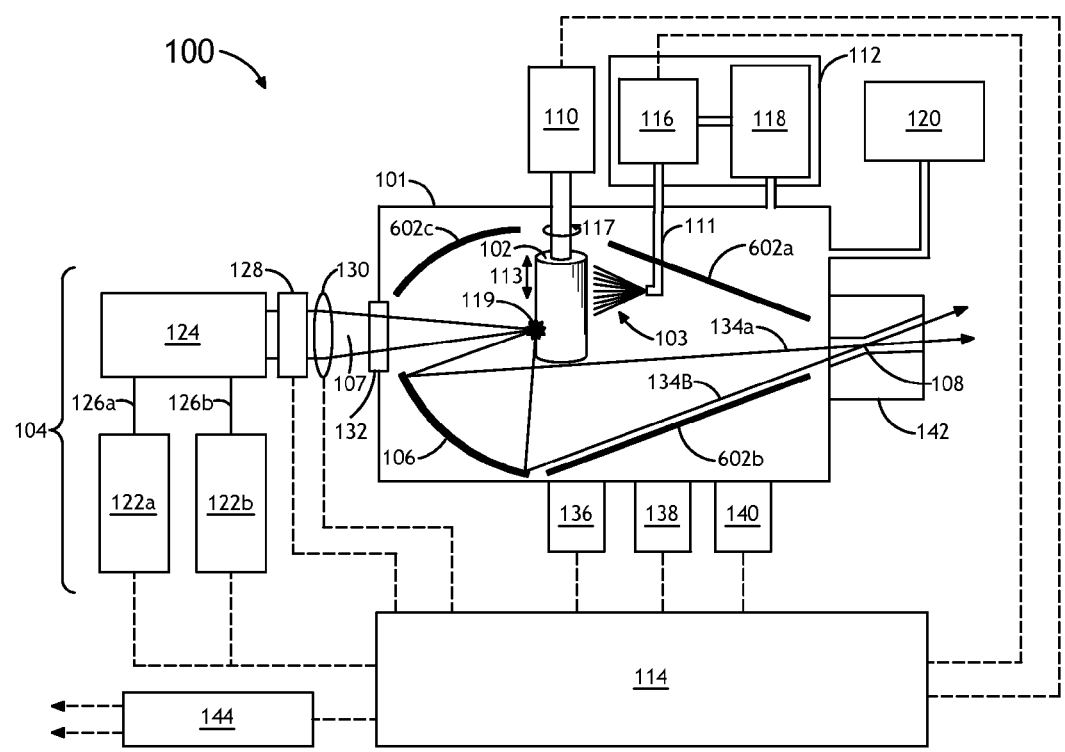
FIG. 6 is a block diagram illustrating an EUV light source equipped with one or more cryogenic panels, in accordance with an embodiment of this disclosure.

FIG. 6 illustrates a block diagram view of the EUV source 100 equipped with one or more cryogenic panes 602a, 602b and/or 602c, in accordance with one or more embodiments of the present invention. It is noted herein that debris from the plasma-forming material (e.g., Xe debris) in the form of fast neutrals, ions and/or as fragments may produce secondary metal debris by sputtering metal plasma materials. Further, condensation of metal debris on the various optical elements within the vacuum chamber 101 (e.g., collection optical element 106, laser focusing optics and the like) may significantly limits system lifetime. It is recognized herein that the implementation of one or more cryogenic panels 602a, 602b and/or 602c may prevent, or at least reduce, degradation of the collection optical element 106 and other optical elements within the vacuum chamber 101. In one embodiment, the one or more cryogenic panels 602a, 602b and/or 602c are installed inside the vacuum chamber 101 and limit plasma-forming debris (e.g., Xe debris) from impinging on any one of the multiple metal surfaces within the vacuum chamber 101. In one embodiment, the one or more cryogenic panels 602a, 602b and/or 602c include one or more panel structures having a thin layer (e.g., 1-10 µm) of plasma-forming material (e.g., Xe) pre-deposited on the surface of the panel structures.

In another embodiment, the source 100 includes a temperature management system 144. In another embodiment, the control system 114 is communicatively coupled to the temperature control system 144 and is configured to control the temperature of the source 100 in response to one or more temperature readings obtained via various temperature measurement devices (not shown) arranged through the source 100. In one embodiment, the temperature management system 144 may include a water jacket for controlling temperature of the vacuum chamber 101. In another embodiment, the temperature management system 144 may include a cryogenic system for controlling temperature of the rotatable, cylindrically-symmetric element 102 and/or the plasma-forming recycling process via system 118.

In another embodiment, the one or more control systems 114 are configured for data acquisition from any one of the various subsystems and measurement devices of the EUV source 100. In another embodiment, the control system 114 may store or log all received data in memory (not shown). In another embodiment, based on one or more signals from the various subsystems, the control system 114 may in turn control or adjust one or more states or conditions of the one or more subsystems (e.g., focusing element 130, actuation device 110, source 104, gas management system 112, vacuum system 120, temperature management system 144 and the like). In another embodiment, the control system 114 may be communicatively coupled to a main control system of an inspection system (e.g., see inspection system 700 and 1200 below) implementing EUV source 100.

Figure 7:
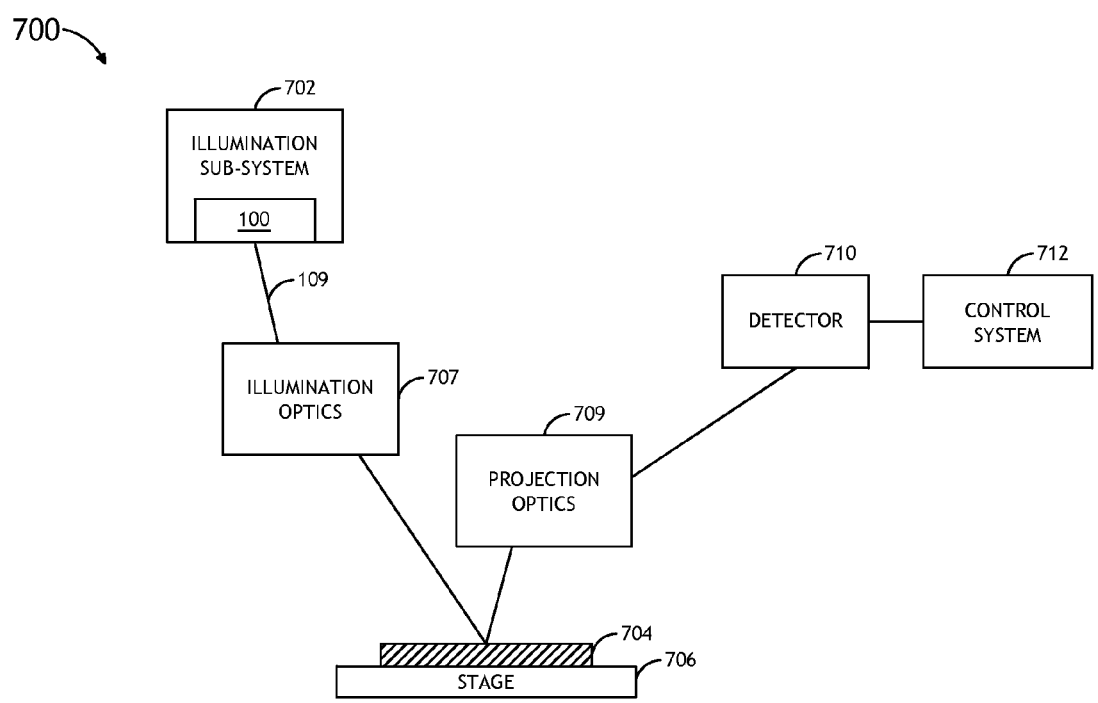
FIG. 7 is a block diagram illustrating an optical system including a plasma-based EUV source, in accordance with an embodiment of this disclosure.

FIG. 7 illustrates a block diagram view of an inspection system 700 incorporating a plasma-based illumination source 100, in accordance with one embodiment of the present invention. In one embodiment, the system 700 includes an illumination sub-system 702. In one embodiment, the illumination sub-system 702 incorporates the EUV light source 100 described throughout the present disclosure. In another embodiment, although not shown in FIG. 7, the system 700 includes a set of illuminator optics. In one embodiment, the illuminator optics may direct illumination 109 emanating from the EUV light source 100 to one or more specimens 704 disposed on a specimen stage 706. For example, the one or more specimens 704 may include, but are not limited to, a wafer (e.g., semiconductor wafer). By way of another example, the one or more specimens 704 may include, but are not limited to, a reticle. In another embodiment, the system 700 includes one or more detectors 710. In another embodiment, the system 700 includes a set of projections optics 709 suitable for collecting light scattered, reflected or otherwise emanating from the specimen 704 and directing the light to the one or more detectors (e.g., CCD, TDI-CCD, PMT and the like). In another embodiment, the system 700 includes a control system 712 for receiving and/or analyzing the measurement results from the detector 710.

In one embodiment, the inspection system 700 is configured as a wafer inspection system or a reticle inspection system. In this regard, the inspection system 700 may include any wafer or reticle inspection optical architecture known in the art suitable for operating in the EUV spectral range. It is further recognized that the inspection system 700 may be configured as EUV mask blank inspection system. EUV-based mask blank inspection is described generally in U.S. Pat. No. 8,711,346 to Stokowski, issued on Apr. 29, 2014, which is incorporated herein by reference in the entirety. EUV-based mask blank inspection is described generally in U.S. patent application Ser. No. 13/417,982 to Xiong et al., filed on Mar. 12, 2012, which is incorporated herein by reference in the entirety. EUV-based reticle inspection is generally described in U.S. patent application Ser. No. 13/905,449 to Nasser-Ghodsi et al., filed on May 30, 2013, which is incorporated herein by reference in the entirety.

In another embodiment, although not shown, the EUV light source 100 described throughout the present invention may be implemented within an EUV lithography system. In one embodiment, the optical lithography system (not shown) may include a set of illuminator optics configured to direct output light from the EUV light source 100 to an EUV-compatible lithography mask (e.g., EUV reflective mask). In another embodiment, the lithography system includes a set of projection optics configured to receive illumination reflected from the mask and direct the reflected illumination from the mask to one or more wafers disposed on a wafer stage. The optical lithography system may include any EUV lithography system known in the art. EUV-based lithography is described generally in U.S. patent application Ser. No. 13/419,042 to Wang, filed on Mar. 13, 2012, which is incorporated herein by reference in the entirety.

FIGS. 8A through 11 illustrate schematic views of a cooled mirror device 800, in accordance with one or more embodiments of the present disclosure. As observed in the collection mirrors in an EUV source, a mirror is often exposed to a significant amount of energy, which is not necessarily uniformly distributed across the given mirror. This non-uniformity is often, but not necessarily, axisymmetric about the center of the mirror, with the spatial heat distribution being relatively stable as a function of time. The cooled mirror device 800 may be utilized to control the temperature of an optical element (e.g., mirror) in a vacuum or low-pressure environment. As discussed further herein, temperature control is accomplished by the cooled mirror device 800 without the need for mechanical contact between the optical element (e.g., mirror) and a corresponding thermal control device, allowing the element to operate with less vibration and/or pressure ripple, among other advantages.

In one embodiment, the cooled mirror device 800 may be implemented within the EUV light source 100 and/or the EUV-based optical system 700 described previously herein. It is noted herein that while the cooled mirror device 800 is described within the context of the EUV light source 100 and the EUV-based optical system 700, the cooled mirror device 800 is not limited to these optical environments. It is recognized herein that the cooled mirror device 800 described throughout the present disclosure may be implemented within any optical system requiring cooling of one or more mirrored surfaces (e.g., collection optics, illuminator optics, projection optics, focusing optics and the like). Further, the cooled mirror device 800 may be implemented within any optical range known in the art. While the cooled mirror device 800 is described in the context of EUV light, it is noted herein that the cooled mirror device 800 may be extended to any optical regime, including, but not limited to, DUV, EUV, UV, Visible, and IR spectral ranges.

In one embodiment, the cooled mirror device 800 includes a mirror assembly 802. In one embodiment, the mirror assembly 802 includes a mirror 801 positioned on a first side (e.g., top side of mirror assembly in FIG. 8) of the mirror assembly 802. In another embodiment, the mirror assembly 802 includes a first plurality of heat transfer elements 803 formed in a first pattern positioned on a second side (e.g., bottom side of mirror assembly in FIG. 8) of the mirror assembly opposite the first side of the mirror assembly 802.

In another embodiment, the cooled mirror device 800 includes a temperature control assembly 804. In one embodiment, the temperature control assembly 804 includes a second plurality of heat transfer elements 805. In one embodiment, the heat transfer elements 805 are formed on a first surface (e.g., top surface of temperature control assembly 804 in FIG. 8). In another embodiment, the second plurality of heat transfer elements 805 of the temperature control assembly are formed in a second pattern. In one embodiment, the second pattern of the second plurality of heat transfer elements 805 is compatible, or matched, to the first pattern of the first plurality of heat transfer elements 803 of the mirror assembly 802. In one embodiment, the heat transfer elements 805 of the temperature control assembly 804 may be arranged such that they are interleaved with the heat transfer elements 803 of the mirror assembly 802. It is further noted that this interleaving may be carried out such that there is no physical contact, or "touching," between the first set of heat transfer elements 803 and the second set of heat transfer elements 805, as shown in FIG. 8.

In this regard, the first plurality of heat transfer elements 803 is configured to transfer heat to the second plurality of heat transfer elements 805 via radiation and/or gas conduction. For example, heat may be transferred between the mirror 801 and the temperature control assembly 805 via radiation, which is enhanced by the increase in surface area between the heat transfer elements 803 and the heat transfer elements 805. Further, heat transfer between the mirror 801 and the temperature control assembly 805 is also facilitated by gas conduction in settings where the surrounding atmosphere has a gas molecule density sufficient to maintain significant gas conduction. For instance, such gas conduction may exist between the first plurality of heat transfer elements 803 and the second plurality of heat transfer elements 805 in pressure regimes of approximately 0.05 to 2,000 Pa or greater.

It is noted herein that providing sufficient spacing between the heat transfer elements 803 of the mirror assembly 802 and the heat transfer elements 805 of the temperature control assembly 804 allows for the adjustment of the position of the mirror 801 (e.g., adjustment for beam steering purposes) without adjusting the position of the temperature control element 804. In addition, sufficient spacing between the heat transfer elements 803 of the mirror assembly 802 and the heat transfer elements 805 of the temperature control assembly 804 provides for vibrational isolation between the temperature control assembly 804 and the mirror assembly 802 by allowing a small amount of relative motion between the mirror assembly 802 and the temperature control assembly 804.

In one embodiment, the second plurality of heat transfer elements 805 may be offset from the first plurality of heat transfer elements 803 by a selected offset distance. In one embodiment, the temperature control assembly 804 may be mechanically coupled to an actuation device (e.g., linear translation device, rotational translation device or a combination thereof). In this regard, an actuation device (not shown) may serve to control, or adjust, the offset distance between the first plurality of heat transfer elements 803 and the second plurality of heat transfer elements 805. In another embodiment, the actuation device is communicatively coupled to a control system (not shown). In one embodiment, the control system may direct the actuation device to control a position of the temperature control assembly relative to the mirror assembly in order to control or adjust the offset distance between the first plurality of heat transfer elements 803 and the second plurality of heat transfer elements 805. For instance, the control system or user may adjust the offset distance between the heat transfer elements 803 and heat transfer elements 805 based on the heat transfer required for the given mirror and/or application.

In this regard, the heat transfer rate between the mirror 801 and the temperature control assembly 804 may be varied as a function of time by moving the temperature control assembly 804 closer to or farther from the mirror assembly 802. As such, slow time-varying changes of the required heat transfer may be made by moving the temperature control element 804, which can provide greater control than merely adjusting the temperature of the given temperature control element (e.g., via a heating or cooling element).

In one embodiment, the heat transfer elements 803 of the mirror assembly 802 and/or the heat transfer element 805 of the temperature control assembly 804 include heat transfer protrusions. For example, as shown in FIG. 8, the heat transfer elements 803 of the mirror assembly 802 and/or the heat transfer element 805 of the temperature control assembly 804 may include heat transfer fins.

In one embodiment, the size or spacing of the heat transfer elements 803 of the mirror assembly 802 and/or the size or spacing of the heat transfer elements 805 of the temperature control assembly 804 may vary spatially across the mirror assembly 802 and/or the temperature control assembly 804. For example, the size (e.g., height and/or thickness) and/or spacing between heat transfer elements 803, 805 may be tuned to enhance local heat transfer control across the mirror assembly 802. For instance, in regions of the mirror 801 that may otherwise exhibit higher temperatures from impinging radiation (e.g., EUV radiation), the heat transfer elements 803, 805 may be larger and/or be more densely spaced can be larger and/or more densely spaced, which provides increased local heat transfer.

In another embodiment, the level of protrusion of the heat transfer elements 803 of mirror assembly 802 and/or the heat transfer elements 805 of the temperature control assembly 804 may vary spatially across the mirror assembly 802 and/or the temperature control assembly 804. For example, as shown in FIG. 8, the extent with which the heat transfer elements 803 of the mirror assembly 802 protrude into the spaces between the heat transfer elements 805 of the temperature control element 804 may vary as a function of position across the mirror assembly 802. For instance, in regions of the mirror 801 that may otherwise exhibit higher temperatures from impinging radiation (e.g., EUV radiation), the heat transfer elements 803 of mirror assembly 802 may protrude more deeply into the spaces between the heat transfer elements 805 of the temperature control assembly 804, which provides increased local heat transfer.

Figure 9:
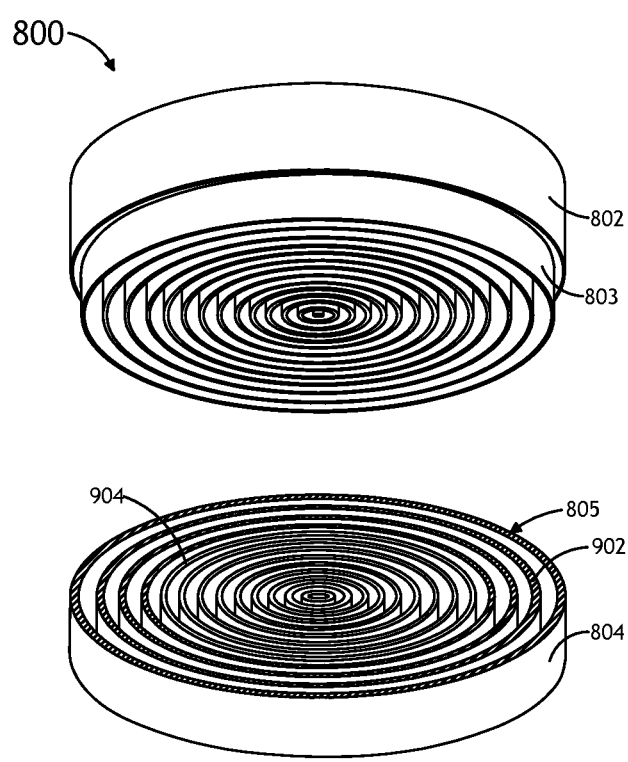
FIG. 9 illustrates an isometric view of a cooled mirror device equipped with multiple coatings having different heat transfer characteristics, in accordance with an embodiment of this disclosure.

FIG. 9 illustrates a schematic view of a cooled mirror device 800 having multiple coatings 902, 904 to control heat transfer as a function of position across the mirror assembly 802 of the device 800, in accordance with one embodiment of the present invention. In one embodiment, the heat transfer elements 803 of the mirror assembly 802 and/or the heat transfer elements 805 of the temperature control assembly 804 are coated with one or more coatings in order to spatially vary heat transfer across the mirror 801. In this regard, different regions of the heat transfer elements 803 of the mirror assembly 802 and/or the heat transfer elements 805 of the temperature control assembly 804 may be treated with different coatings, which possess different heat transfer characteristics. For example, radiation heat transfer can be customized as a function of position across the mirror assembly 802 by using coatings of different emissivities in different regions of the mirror assembly 802 and/or temperature control element 804, without impacting the heat transfer via gas conduction (if present).

For instance, as shown in FIG. 9, a first coating 904 having a first emissivity disposed on a grouping of inner annular rings may have a higher radiative heat transfer characteristic than a group of outer annular rings coated with a second coating 902 having a second emissivity, thereby leading to a larger degree of heat transfer at the center of the mirror assembly 802 than at the edges of the mirror assembly 802.

Figure 10:
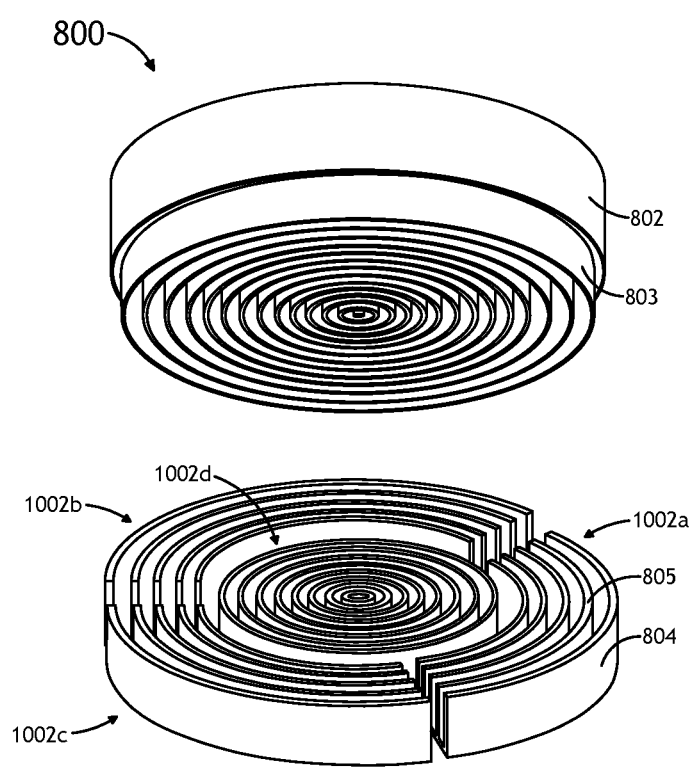
FIG. 10 illustrates an isometric view of a cooled mirror device equipped with multiple segments having different heat transfer characteristics, in accordance with an embodiment of this disclosure.

FIG. 10 illustrates a schematic view of a cooled mirror device 800 having multiple segments 1002a-1002d to control heat transfer as a function of position across the mirror assembly 802 of the device 800, in accordance with one embodiment of the present invention. In one embodiment, the heat transfer elements 803 of the mirror assembly 802 and/or the heat transfer elements 805 of the temperature control assembly 804 include multiple segments 1002a-1002d in order to spatially vary heat transfer across the mirror 801. In this regard, different segments 1002a-1002d of the heat transfer elements 803 of the mirror assembly 802 and/or the heat transfer elements 805 of the temperature control assembly 804 may possess one or more different structural characteristics, which cause at least some of the different segments 1002a-1002d to display different heat transfer characteristics. For example, the varying structural characteristics of the different segments 1002a-1002d may include, but are not limited to, spacing, size, protrusion level and construction material of the heat transfer elements 803 of the mirror assembly 802 and/or the heat transfer elements 805 of the temperature control assembly 804. In another embodiment, at least some of the segments 1002a-1002d are independently actuatable. For example, each of the segments 1002a-1002d may be coupled to a dedicated actuation device, which in turn is controlled by a control system (not shown). In this regard, the control system may independently control the offset distance between a given segment 1002a, 1002b, 1002c or 1002d of a temperature control assembly 804 and the mirror assembly 802. Such an arrangement allows for the fine tuning of heat transfer as a function of position across the mirror assembly 802.

Figure 8A:
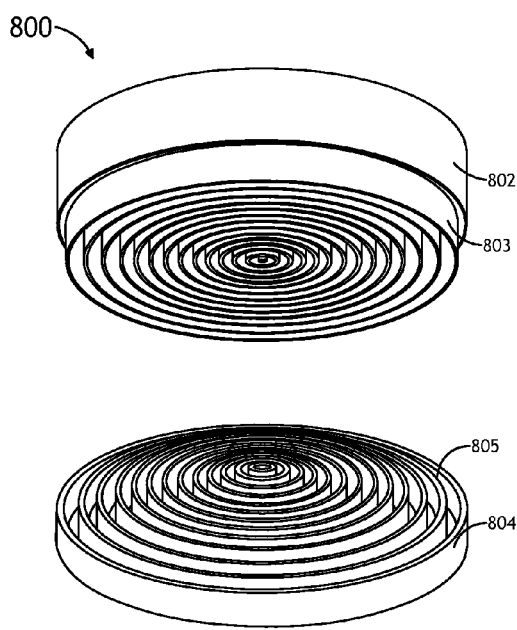
FIG. 8A illustrates an isometric view of a cooled mirror device having heat transfer elements arranged in an axisymmetric configuration, in accordance with an embodiment of this disclosure.
Figure 8B:
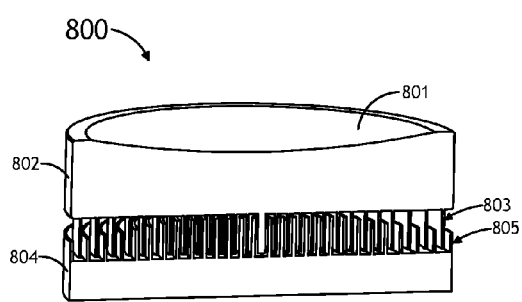
FIG. 8B illustrates a cross-sectional view of a cooled mirror device having heat transfer elements arranged in an axisymmetric configuration, in accordance with an embodiment of this disclosure.

In one embodiment, as shown in FIGS. 8A-10, the heat transfer elements 803, 805 of the mirror assembly 802 and/or the temperature control assembly 804 may include axisymmetrically arranged heat transfer fins. For example, as shown in FIG. 8, the heat transfer fins of the mirror assembly 802 and/or the temperature control assembly 804 may include annular fins formed concentrically across the mirror assembly 802 and/or the temperature control assembly 804.

Figure 11A:
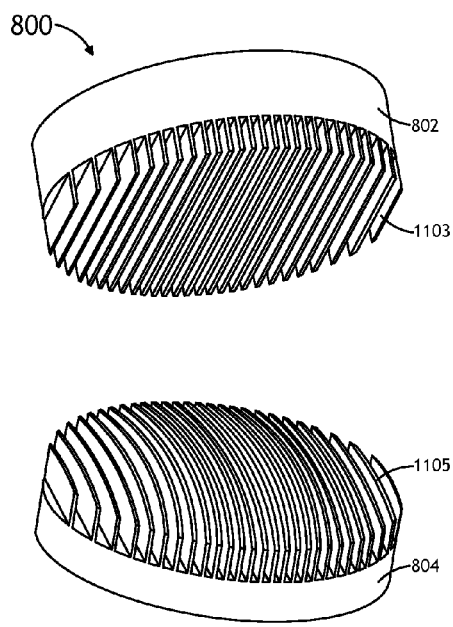
FIG. 11A illustrates an isometric view of a cooled mirror device having heat transfer elements arranged in a parallel configuration, in accordance with an embodiment of this disclosure.
Figure 11B:
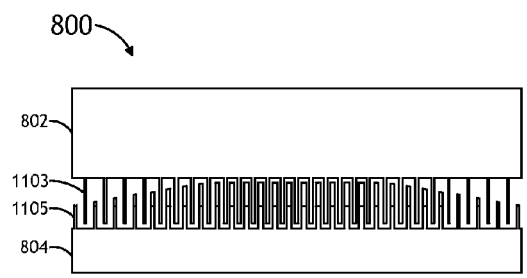
FIG. 11B illustrates a cross-sectional view of a cooled mirror device having heat transfer elements arranged in a parallel configuration, in accordance with an embodiment of this disclosure.

In another embodiment, as shown in FIGS. 11a and 11b, the heat transfer elements 803, 805 of the mirror assembly 802 and/or the temperature control assembly 804 may include parallel arranged heat transfer fins. For example, the heat transfer fins of the mirror assembly 802 and/or the temperature control assembly 804 may include a linear arrangement of fins formed across the mirror assembly 802 and/or the temperature control assembly 804.

It is noted herein that the above examples do not represent limitations on the present invention and are provided merely for illustrative purposes. It is recognized herein that the heat transfer elements (or fins) of the present invention may take on any geometric shape (or portion of geometrical shape) known in the art such as, but not limited to, concentrically arranged annular fins, concentrically arranged elliptical fins, concentrically arranged polygonal fins, linearly spaced fins, non-linearly spaced fins, groups of linearly spaced fins and the like. Further, it is recognized herein that the fins of the present invention need not be uniform. For example, a given fin may vary in thickness as a function of height.

It is recognized herein that in cases where the interleaving fins are axisymmetric, such as FIGS. 8A-10, the mirror assembly 802 and the temperature assembly 804 must be moved normal to the nominal plane on which the fins reside. In some applications, it may be advantageous to remove the mirror assembly laterally (i.e., in a direction parallel to the nominal plane on which the fins reside) rather than normally. In this case, the fins may be arranged such they are all parallel to the desired direction of extraction, as shown in FIGS. 11A and 11B.

In one embodiment, the mirror 801 of the cooled mirror device 800 may include any mirror known in the art. For example, the mirror 801 may include, but is not limited to, a mirror suitable for use with EUV light. For instance, the mirror 801 may include, but is not limited to, a multilayer EUV mirror.

Figure 12:
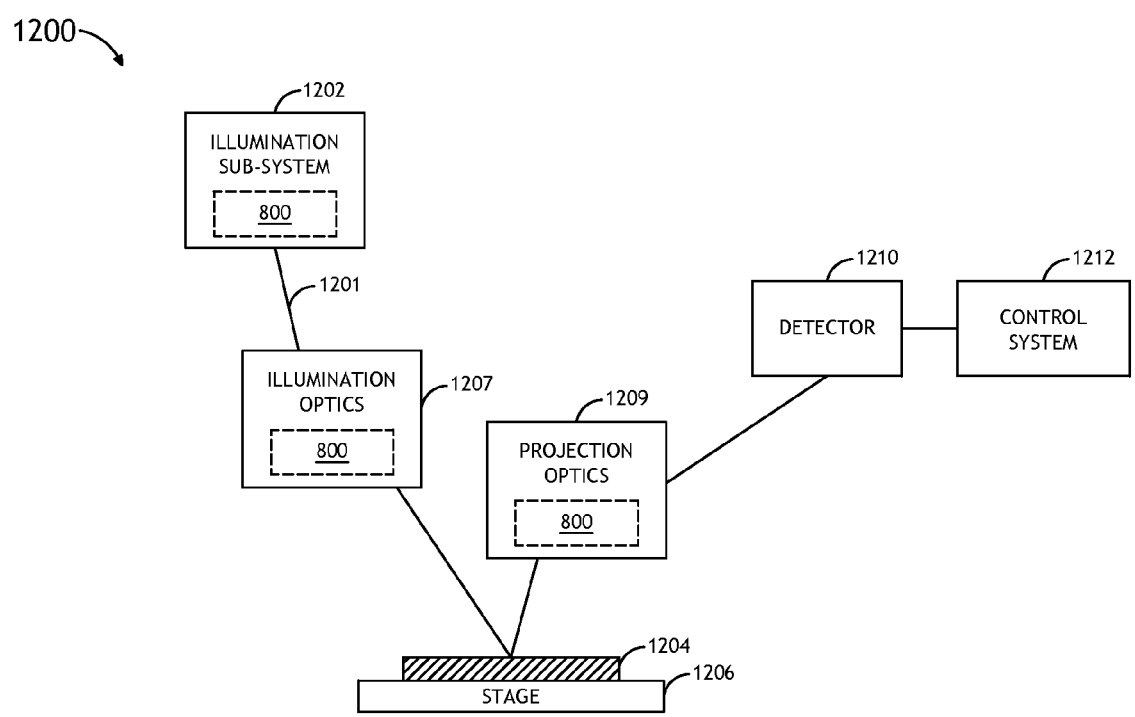
FIG. 12 is a block diagram illustrating an optical system including one or more cooled mirror devices, in accordance with an embodiment of this disclosure.

FIG. 12 illustrates a block diagram view of an inspection system 1200 incorporating one or more cooled mirror devices 800, in accordance with one embodiment of the present invention.

In one embodiment, the system 800 includes an illumination sub-system 1202. In one embodiment, the illumination sub-system 1202 includes an illumination source (e.g., plasma-based EUV source, such as, but not limited to, source 100). In another embodiment, the illumination sub-system 1202 includes a set of collection optics including one or more mirrors configured to collect illumination from an illumination source. For example, one or more of the collection mirrors of illumination sub-system 1202 may include a cooled mirror device 800.

In another embodiment, the system 1200 includes a set of illuminator optics 1207 including one or more mirrors configured to direct illumination 1201 from the one or more mirrors of the collection optics to one or more specimens 1204 disposed on stage 1206. For example, the one or more specimens 1204 may include, but are not limited to, a wafer (e.g., semiconductor wafer). By way of another example, the one or more specimens 1204 may include, but are not limited to, a reticle. For example, one or more of the illuminator mirrors of the illumination optics 1207 may include a cooled mirror device 800.

In another embodiment, the system 1200 includes a set of projection optics 1209 including one or more mirrors suitable for collecting light scattered, reflected or otherwise emanating from the specimen 1204 and directing the light to the one or more detectors 1210 (e.g., CCD, TDI-CCD, PMT and the like). For example, one or more of the mirrors of the projection optics 1209 may include a cooled mirror device 800.

In one embodiment, although not shown in FIG. 12, the cooled mirror device 800 may be utilized as a mirror of one or more focusing optics in a mask inspection system (e.g., EUV mask inspection system). In another embodiment, the cooled mirror device 800 may be utilized as a mirror of one or more focusing optics in a wafer inspection system (e.g., EUV wafer inspection system). In another embodiment, the cooled mirror device 800 may be utilized as a mirror of one or more focusing optics in a lithography system (e.g., EUV lithography system).

In another embodiment, the system 1200 includes a control system 1212 for receiving and/or analyzing the measurement results from the detector 1210.

In one embodiment, the inspection system 1200 is configured as a wafer inspection system or a reticle inspection system. In this regard, the inspection system 1200 may include any wafer or reticle inspection optical architecture known in the art suitable for operating in any spectral range (e.g., EUV spectral range). It is further recognized that the inspection system 1200 may be configured as EUV mask blank inspection system. EUV-based mask blank inspection is described generally in U.S. Pat. No. 8,711,346 to Stokowski, issued on Apr. 29, 2014, which is incorporated above by reference in the entirety. EUV-based mask blank inspection is described generally in U.S. patent application Ser. No. 13/417,982 to Xiong et al., filed on Mar. 12, 2012, which is incorporated above by reference in the entirety. EUV-based reticle inspection is generally described in U.S. patent application Ser. No. 13/905,449 to Nasser-Ghodsi et al., filed on May 30, 2013, which is incorporated above by reference in the entirety.

Those having skill in the art will appreciate that there are various vehicles by which processes and/or systems and/or other technologies described herein can be embodied (e.g., hardware, software, and/or firmware), and that the preferred vehicle will vary with the context in which the processes and/or systems and/or other technologies are deployed. In some embodiments, various steps, functions, and/or operations are carried out by one or more of the following: electronic circuits, logic gates, multiplexers, programmable logic devices, ASICs, analog or digital controls/switches, microcontrollers, or one or more control systems (e.g., control system 114, control system 712 or control system 1212). A control system may include a computing system including, but not limited to, a personal computing system, mainframe computing system, workstation, image computer, parallel processor, or any other computational/control device known in the art. In general, the terms "control system" and "controller" (e.g., control system 114, control system 712 or control system 1212) are broadly defined to encompass any device having one or more processors, which execute program instructions from a carrier medium (e.g., memory). Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a solid state memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. An apparatus for generating extreme ultra-violet (EUV) light comprising:
    a vacuum chamber;
    a rotatable, cylindrically-symmetric element having a surface at least partially coated with a plasma-forming target material and disposed within the vacuum chamber;
    one or more actuation devices configured to control at least one of an axial position or a tilt of the rotatable, cylindrically-symmetric element;
    a drive laser source configured to generate one or more laser pulses sufficient to generate EUV light via formation of a plasma by excitation of the plasma-forming target material;
    a set of focusing optics configured to focus the one or more laser pulses onto a portion of the surface of the rotatable, cylindrically-symmetric element;
    a set of collection optics configured to receive EUV light emanated from the plasma generated in response to the excitation of the plasma-forming target material and further configured to direct the illumination to an intermediate focal point; and
    a gas management system including a gas supply subsystem configured to supply plasma-forming target material to the surface of the rotatable, cylindrically-symmetric element.

2. The apparatus of claim 1, wherein the rotatable, cylindrically-symmetric element comprises:
    a cylinder.

3. The apparatus of claim 1, wherein the one or more laser pulses comprises:
    a series of laser pulses sufficient to generate EUV light via excitation of a portion of the plasma-forming target material.

4. The apparatus of claim 3, wherein the series of laser pulses sufficient to generate EUV light via excitation of a portion of the plasma-forming target material includes:
    one or more pre-pulses sufficient to non-thermally ablate a portion of the plasma-forming target material; and
    one or more main pulses sufficient to generate EUV light via excitation of a portion of the non-thermally ablated portion of the plasma-forming target material.

5. The apparatus of claim 1, wherein the one or more laser pulses have a duration in the rage of 5 to 50 ns.

6. The apparatus of claim 1, wherein the one or more laser pulses are repeatedly produced at a frequency in the range of 1 to 50 kHz.

7. The apparatus of claim 1, wherein the drive laser source comprises:
    one or more drive lasers.

8. The apparatus of claim 7, wherein the drive laser source comprises:
    a first drive laser;
    at least one additional drive laser; and
    a beam combiner to combine a series of pulses generated by the first drive laser with a series of pulses generated by the at least one additional drive laser into a series of combined laser pulses.

9. The apparatus of claim 1, wherein the one or more actuation devices is configured to control a rotational state of the rotatable, cylindrically-symmetric element.

10. The apparatus of claim 9, further comprising:
    a control system in communication with the one or more actuation devices, the control system configured to cause the one or more actuation devices to perform a pulsed axial translation process.

11. The apparatus of claim 10, wherein the pulsed axial translation process comprises:
    aligning the drive laser source at a first axial position of the rotatable, cylindrically-symmetric element;
    rotating the rotatable, cylindrically-symmetric element to cause the one or more laser pulses of the drive laser source to traverse the circumference of the rotatable, cylindrically-symmetric element along the first axial position; and
    axially translating the rotatable, cylindrically-symmetric element relative to the drive laser source following a full rotation of the rotatable, cylindrically-symmetric element so to align the drive laser source at a second axial position of the rotatable, cylindrically-symmetric element; and
    rotating the rotatable, cylindrically-symmetric element to cause the one or more laser pulses of the drive laser source to traverse the circumference of the rotatable, cylindrically-symmetric element along the second axial position.

12. The apparatus of claim 10, wherein the pulsed axial translation process comprises:
    performing a series of pulsed axial translations on a downward stroke of the rotatable, cylindrically-symmetric element; and
    performing a series of pulsed axial translations on an upward stroke of rotatable, cylindrically-symmetric element, wherein the axial positions associated with the series of pulsed axial translations on the downward stroke are interlaced with the axial positions associated with the series of pulsed axial translations on the upward stroke.

13. The apparatus of claim 1, further comprising:
    a beam diagnostic subsystem configured to monitor one or more characteristics of the one or more laser pulses generated by the drive laser source; and
    a control system configured to receive the one or more monitored parameters from the beam diagnostic subsystem, the control system further configured to adjust at least one of one or more parameters of the drive laser source, one or more parameters of the rotatable, cylindrically-symmetric element, one or more parameters of the vacuum chamber, one or more parameters of the set of focusing optics and one or more parameters of the gas supply subsystem.

14. The apparatus of claim 1, further comprising:
one or more focusing optics configured to actively focus the one or more laser pulses from the drive laser source onto a plasma generation region of the rotatable, cylindrically-symmetric element; and
a control system communicatively coupled to the one or more focusing optics and configured to adjust the focus of the one or more laser pulses from the drive laser source.

15. The apparatus of claim 1, wherein the gas management system further includes:
a plasma-forming material recycling subsystem.

16. The apparatus of claim 1, wherein the rotatable, cylindrically-symmetric element comprises:
a conductive rotatable, cylindrically-symmetric element having a reflective surface being substantially reflective to the one or more pulses of the drive laser source.

17. The apparatus of claim 1, wherein the rotatable, cylindrically-symmetric element comprises:
a conductive rotatable, cylindrically-symmetric element being substantially transparent to the one or more laser pulses of the drive laser source.

18. The apparatus of claim 1, wherein the rotatable, cylindrically-symmetric element includes a plurality of mass-limited targets embedded within the surface of the rotatable, cylindrically-symmetric element.

19. The apparatus of claim 1, wherein the rotatable, cylindrically-symmetric element includes a plurality of adhesion structures within the surface of the rotatable, cylindrically-symmetric element.

20. The apparatus of claim 1, further comprising:
one or more cryogenic panels disposed within the vacuum chamber and configured to shield one or more metal surfaces within the vacuum chamber from energetic ionic or neutral species of the plasma-forming material.

21. The apparatus of claim 1, further comprising:
one or more EUV diagnostic tools configured to monitor one or more characteristics of generated EUV light; and
a control system configured to receive the one or more monitored parameters from the one or more EUV diagnostic tools, the control system further configured to adjust at least one of plasma position on rotatable, cylindrically-symmetric element and the primary focus of the collection optics.

22. An inspection system comprising:
an illumination sub-system including:
a vacuum chamber;
a rotatable, cylindrically-symmetric element having a surface at least partially coated with a plasma-forming target material and disposed within the vacuum chamber;
one or more actuation devices configured to control at least one of an axial position or a tilt of the rotatable, cylindrically-symmetric element;
a drive laser source configured to generate one or more laser pulses sufficient to generate EUV light via formation of a plasma by excitation of the plasma-forming target material;
a set of focusing optics configured to focus the one or more laser pulses onto a portion of the surface of the rotatable, cylindrically-symmetric element;
a set of collection optics configured to receive EUV light emanated from the plasma generated in response to the excitation of the plasma-forming target material and further configured to direct the illumination to an intermediate focal point;
a gas management system including a gas supply subsystem configured to supply plasma-forming target material to the surface of the rotatable, cylindrically-symmetric element;
a set of illuminator optics configured to direct illumination from the one or more collection optical elements to one or more specimens;
a detector; and
a set of projection optics configured to receive illumination from the surface of the one or more specimens and direct the illumination from the one or more specimens to the detector.

23. The inspection system of claim 22, wherein the inspection system is configured as a wafer inspection system.

24. The inspection system of claim 22, wherein the inspection system is configured as a mask inspection system.

25. The inspection system of claim 22, wherein the illumination includes extreme ultraviolet light.

\* \* \* \* \*